(12) United States Patent
Albrecht et al.

(10) Patent No.: US 8,684,975 B2
(45) Date of Patent: Apr. 1, 2014

(54) INSTRUMENT SEAL

(75) Inventors: Jeremy J. Albrecht, Ladera Ranch, CA (US); John R. Brustad, Rancho Santa Margarita, CA (US); Gary M. Johnson, Rancho Santa Margarita, CA (US); Matthew W. Becerra, Rancho Santa Margarita, CA (US); Eric Nguyen, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 13/419,628

(22) Filed: Mar. 14, 2012

(65) Prior Publication Data
US 2012/0172807 A1 Jul. 5, 2012

Related U.S. Application Data

(63) Continuation of application No. 12/405,040, filed on Mar. 16, 2009, now Pat. No. 8,152,773.

(60) Provisional application No. 61/036,838, filed on Mar. 14, 2008.

(51) Int. Cl.
*A61M 5/178* (2006.01)

(52) U.S. Cl.
USPC ............. 604/167.06; 604/167.01; 604/164.01

(58) Field of Classification Search
USPC ........................... 604/164.01, 167.01–167.06
See application file for complete search history.

(56) References Cited

U.S. PATENT DOCUMENTS

| | | | |
|---|---|---|---|
| 5,201,714 A | 4/1993 | Gentelia et al. | |
| 5,308,336 A | 5/1994 | Hart et al. | |
| 5,342,315 A | 8/1994 | Rowe et al. | |
| 5,360,417 A | 11/1994 | Gravener et al. | |
| 5,429,609 A | 7/1995 | Yoon | |
| 5,441,486 A | 8/1995 | Yoon | |
| 5,752,938 A | 5/1998 | Flatland et al. | |
| 5,782,817 A | 7/1998 | Franzel et al. | |
| 5,788,676 A | 8/1998 | Yoon | |
| 5,865,807 A | 2/1999 | Blake, III | |
| 5,989,233 A | 11/1999 | Yoon | |
| 6,238,373 B1 | 5/2001 | De la Torre et al. | |
| 7,390,317 B2 | 6/2008 | Taylor et al. | |
| 2004/0106942 A1* | 6/2004 | Taylor et al. ................. | 606/185 |
| 2004/0167559 A1 | 8/2004 | Taylor et al. | |
| 2004/0254426 A1 | 12/2004 | Wenchell | |
| 2008/0051733 A1 | 2/2008 | Lynn | |
| 2009/0024097 A1 | 1/2009 | Okoniewski | |

FOREIGN PATENT DOCUMENTS

EP 1 698 291 9/2006

OTHER PUBLICATIONS

European Patent Office, The extended European Search Report for European Patent Application No. EP12178235.3, dated Sep. 20, 2012, entitled "Instrument Seal".

European Patent Office, The International Search Report and the Written Opinion of International Patent Application No. PCT/US09/037295, dated May 6, 2009, entitled "Instrument Seal".

International Bureau of WIPO, International Preliminary Report on Patentability for International Patent Application No. PCT/US2009/037295, dated Sep. 14, 2010, title: Instrument Seal.

* cited by examiner

*Primary Examiner* — Victoria P Shumate
(74) *Attorney, Agent, or Firm* — Patrick Y Ikehara

(57) ABSTRACT

A surgical access port comprises a valve or instrument seal that separates the instrument contact function from the instrument conforming function. Embodiments of the instrument seal comprise in instrument contact element that extends through an opening in a compression element, thereby defining an instrument orifice that seals with an instrument extending therethrough. Embodiments of the instrument contact element comprise a non-distensible membrane or film, for example, as a tube or cylinder.

19 Claims, 17 Drawing Sheets

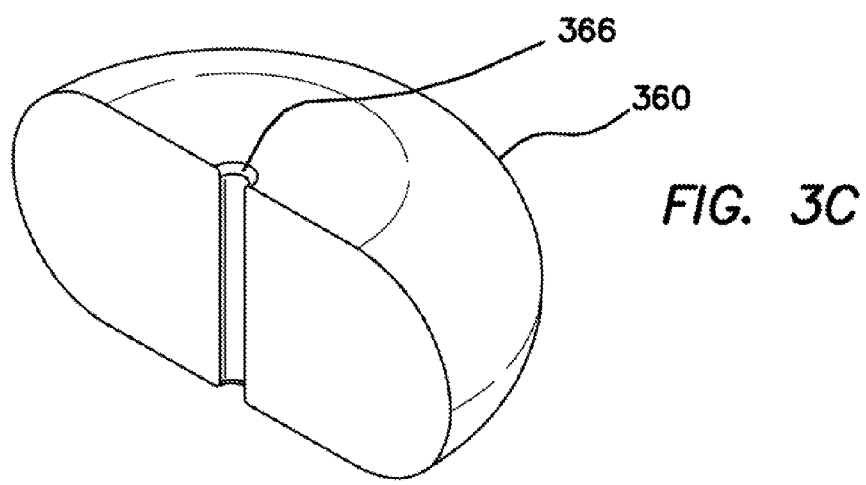
FIG. 3C
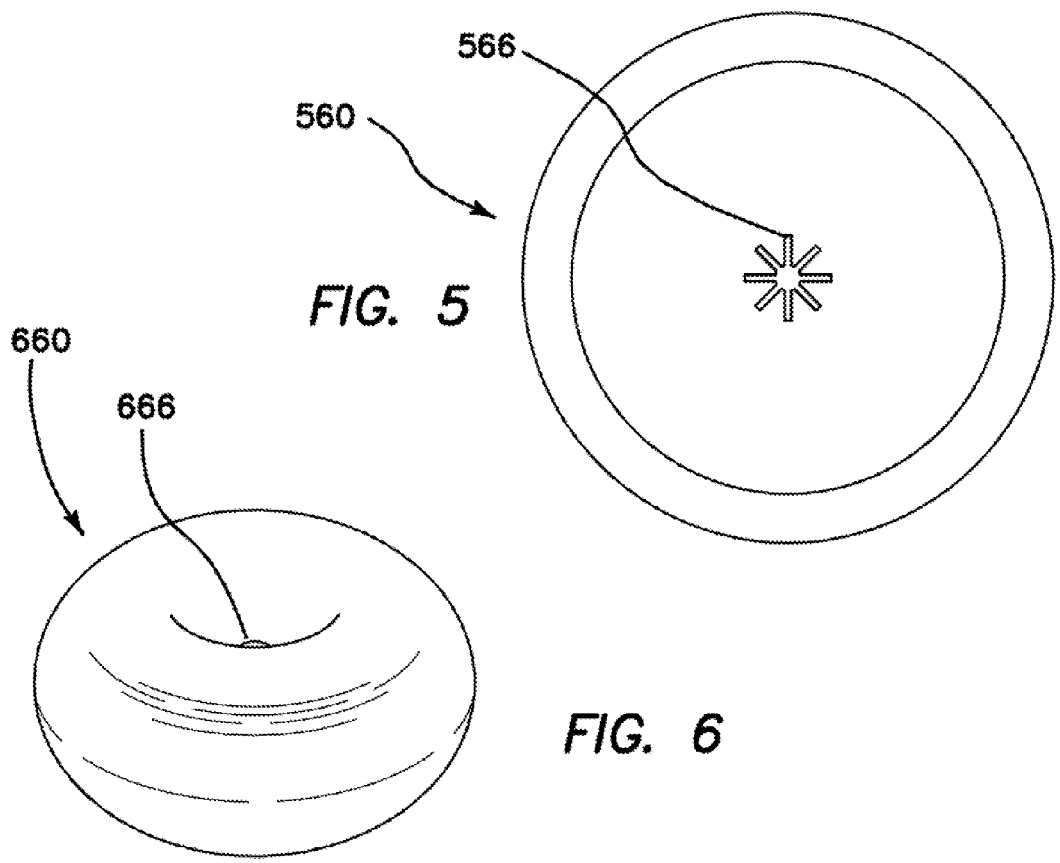
FIG. 5
FIG. 6

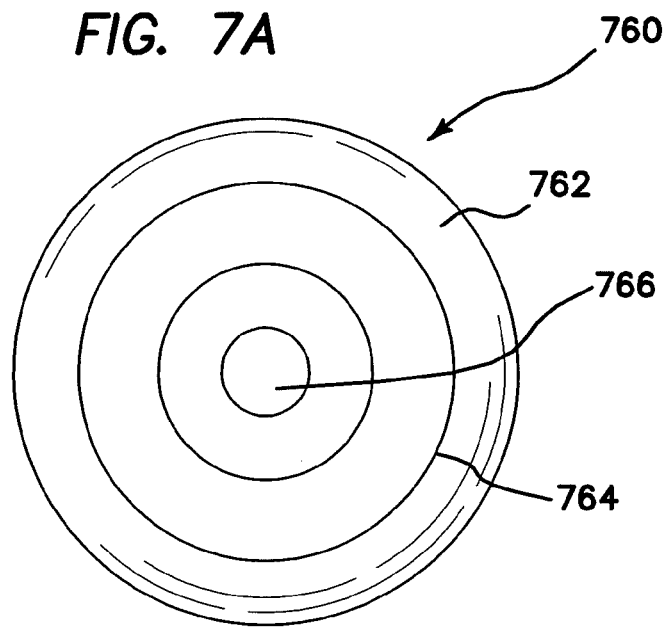
FIG. 7A
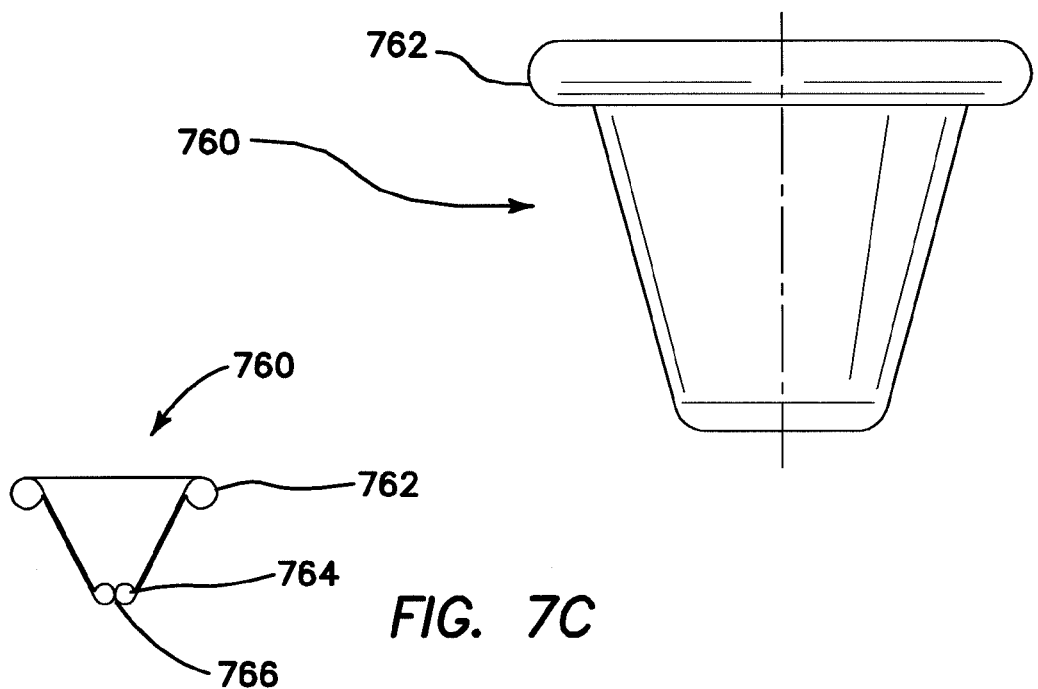
FIG. 7B
FIG. 7C

INSTRUMENT SEAL

CROSS-REFERENCE TO RELATED APPLICATION

This is application is a continuation of U.S. patent application Ser. No. 12/405,040, filed Mar. 16, 2009, now U.S. Pat. No. 8,152,773, issued on Apr. 10, 2012, which claims the benefit of U.S. Application No. 61/036,838, filed Mar. 14, 2008, the entire disclosures of which are incorporated by reference.

BACKGROUND

1. Technical Field

This application generally relates to a medical device, and more particularly, to a surgical access device comprising a seal comprising an instrument contact element extending through a compression element.

2. Description of the Related Art

Minimally invasive surgery is a type of surgery in which instruments access the interior of a patient's body through one or more surgical access devices traversing a body wall. Laparoscopic surgery is a type of minimally invasive surgery. Surgical access devices used in minimally invasive surgery include trocars or cannulas, single ports, and hand ports. Instruments access the interior of the patient's body through an instrument access channel in the access device, which includes a valve or seal that forms a seal with the instrument.

In some cases, a surgical procedure is performed in a body cavity inflated or insufflated with an insufflation gas, for example, carbon dioxide, which lifts an overlying body wall away from an organ bed within the body cavity, thereby providing a surgeon with a less obstructed surgical field. Where the body cavity is the abdomen, the insufflated condition is referred to as "pneumoperitoneum". Surgical access devices used under pneumoperitoneum seal the access channel both in the presence and the absence of instruments extending therethrough, thereby preventing loss of pneumoperitoneum.

A typical trocar seal includes an elastic septum seal and a shield that protects the septum seal from damage, for example, tears and/or punctures, from contact with instruments. Typical septum shields and/or protectors, however, do not protect the orifice of the septum from damage. An exposed portion of the septum seal around the orifice directly contacts and seals against the instrument. Exposing the edge of the septum around the orifice to an instrument exposes a vulnerable portion of the seal to aggressive surface features found on some instruments. The exposed portion of the septum seal around the orifice is placed under immense stress while an instrument is inserted through the trocar, making the material around the orifice susceptible to nicks or cuts caused by contact with surgical instruments, particularly instruments that include sharp edges, undercuts, protuberances, and/or other challenging geometries.

Numerous technical challenges confront those designing and manufacturing septum seals, for example, handling irregularly shaped surgical instruments, and balancing durability with drag force or friction between the seal and surgical instruments. Elastomeric seal materials elongate when instruments are inserted, thereby increasing drag force. For example, a thick septum is resilient and durable, but exhibits a high instrument drag force from overcoming the restoring force generated by expanding a small diameter orifice with a large diameter instrument. Oil canning, or inversion, of typical septum seals can also result in loss of precise instrument movement because the surgeon experiences a different feedback or feel between large and small changes in the position of the instrument. An hour-glass-shaped septum seal can be stretched during instrument insertion, which also increases the drag force.

SUMMARY OF THE INVENTION

A surgical access port comprises a valve or instrument seal that separates the instrument contact function from the instrument conforming function. Embodiments of the instrument seal comprise in instrument contact element that extends through an opening in a compression element, thereby defining an instrument orifice that seals with an instrument extending therethrough. Embodiments of the instrument contact element comprise a non-distensible membrane or film, for example, as a tube or cylinder. Some embodiments of the instrument contact element have an hourglass configuration with a first end proximal of the opening of the compression element and a second end distal of the opening of the compression element. Other embodiments of the instrument contact element "wrap around" the opening in the compression element, with the first end and the second end secured to the same side of the opening, for example, proximal of the opening. Embodiments of the compression element comprise an elastomeric seal, for example, a septum seal and/or a gel seal.

Some embodiments provide a surgical access device comprising an instrument seal, the instrument seal comprising: a longitudinal axis along extending from a proximal end to a distal end; an instrument access channel extending along the longitudinal axis; a seal housing; an elastic compression element disposed in the seal housing, comprising an opening aligned with the access channel; and a non-distensible instrument contact element disposed on the compression element and extending through the opening in the compression element, thereby defining an instrument orifice. The instrument seal has a first state in the absence of an instrument extending through the orifice, and the instrument seal has a second state in the presence of an instrument extending through the orifice in which the instrument contact element seals against the instrument.

In some embodiments, the elastic compression element comprises a septum seal. In some embodiments, the elastic compression element comprises polyisoprene. In some embodiments, an elongation of the elastic compression element is at least about 600%.

In some embodiments, the instrument contact element comprises a polyolefin film. In some embodiments, the instrument contact element is substantially cylindrical in an unconstrained state. In some embodiments, a smallest constrained diameter of the instrument contact element is at least at large as a diameter of a largest instrument that the instrument seal is designed to accommodate.

In some embodiments, the surgical access device is a trocar comprising a seal assembly comprising the instrument seal; and a cannula extending from the seal assembly, wherein the access channel extends through the seal assembly and the cannula. Some embodiments further comprise a zero seal aligned with the access channel.

Some embodiments provide a surgical access device comprising an instrument seal, the instrument seal comprising: a longitudinal axis along extending from a proximal end to a distal end; an instrument access channel extending along the longitudinal axis; a seal housing; an elastomeric compression element disposed in the seal housing; and a non-distensible instrument contact element extending from the proximal end to the distal end of the instrument seal, and through the compression element defining an orifice through which the access channel extends. The instrument seal has a first state in the absence of an instrument extending through the orifice, and the instrument seal has a second state in the presence of an instrument extending through the orifice in which the instrument contact element seals against the instrument.

In some embodiments, surgical access device is a trocar comprising a seal assembly comprising the instrument seal; and a cannula extending from the seal assembly, wherein the access channel extends through the seal assembly and the cannula. In some embodiments, the surgical access device is a hand port.

In some embodiments, the compression element comprises a gel material. In some embodiments, the gel material has an elongation of at least about 1,000%. In some embodiments, the compression element comprises a plurality elastic elements defining an opening through with the instrument contact element extends, wherein least some elastic elements overlap at least one other elastic element. In some embodiments, the compression element comprises a septum seal. In some embodiments, the compression element is disc-shaped. In some embodiments, the compression element is toroidal. In some embodiments, the compression element is tethered to the seal housing.

In some embodiments, the instrument contact element comprises a polyolefin film. In some embodiments, the instrument contact element is substantially cylindrical in an unconstrained state. In some embodiments, the instrument contact element comprises at least one slit. Some embodiments further comprise a lubricant disposed on at least a portion of the instrument contact element. In some embodiments, a distal end of the instrument contact element is secured to a disk weight.

In some embodiments, in the first state, the instrument seal is a zero seal. In some embodiments, in the first state, the instrument contact element at the orifice comprises a plurality of folds.

In some embodiments, the instrument seal has a leak rate of less than about 500 mL/min at 2 kPa in the second state.

Some embodiments further comprise a zero seal through which the access channel extends.

In some embodiments, in the second state, the instrument contact element spaces the instrument from the compression element.

Some embodiments provide a surgical access device comprising an instrument seal, the instrument seal comprising: a longitudinal axis along extending from a proximal end to a distal end; an instrument access channel extending along the longitudinal axis; a seal housing; a tubular instrument contact element longitudinally disposed in the seal housing, through which the access channel extends; and an elastic compression element disposed around the instrument contact element, compressing a portion thereof, thereby defining an orifice. A smallest uncompressed diameter of the instrument contact element is at least at large as a diameter of a largest instrument that the instrument seal is designed to accommodate, the instrument seal has a first state in the absence of an instrument extending through the orifice, and the instrument seal has a second state in the presence of an instrument extending through the orifice in which the instrument contact element seals against the instrument.

In some embodiments, the instrument contact element comprises a non-distensible material. In some embodiments, the non-distensible material comprises a polyolefin film. In some embodiments, the instrument contact element comprises an elastomeric material.

Some embodiments provide a surgical access device comprising an instrument seal, the instrument seal comprising: a longitudinal axis along extending from a proximal end to a distal end; an instrument access channel extending along the longitudinal axis; a seal housing; a tubular instrument contact element longitudinally disposed in the seal housing, and through which the access channel extends, the instrument contact element comprising a first end operatively coupled to the seal housing and a second end floating within the seal housing; and an elastic compression element disposed around the instrument contact element, compressing a portion thereof, thereby defining an orifice, and secured within the seal housing by the instrument contact element. The instrument seal has a first state in the absence of an instrument extending through the orifice, and the instrument seal has a second state in the presence of an instrument extending through the orifice in which the instrument contact element seals against the instrument.

BRIEF DESCRIPTION OF THE DRAWINGS

FIG. 3C is a cut-away view of a compression element of the seal assembly illustrated in FIG. 3B.

FIG. 5 is a top view of an embodiment of an embodiment of a compression element comprising a star-shaped opening.

FIG. 6 is a perspective view of an embodiment of an embodiment of a toroidal compression element.

FIGS. 7A, 7B, and 7C are top, side, and cross-sectional views of an embodiment of a frustoconical compression element.

Similar elements have similar reference numbers.

DETAILED DESCRIPTION OF CERTAIN EMBODIMENTS

A valve or seal for a surgical access device comprises an instrument contact element and a compression element. Separating the instrument contact and the instrument conforming functions of the seal into separate components permits improving each function independently of the other, for example, through material selection, dimensioning, changes in geometry, and the like. For example, one material may exhibit high puncture resistance and low friction, while a second material exhibits high elongation and low modulus. Embodiments of the seal are useful in surgical access devices such as trocars, hand ports, single ports, and the like.

Figure 1A:
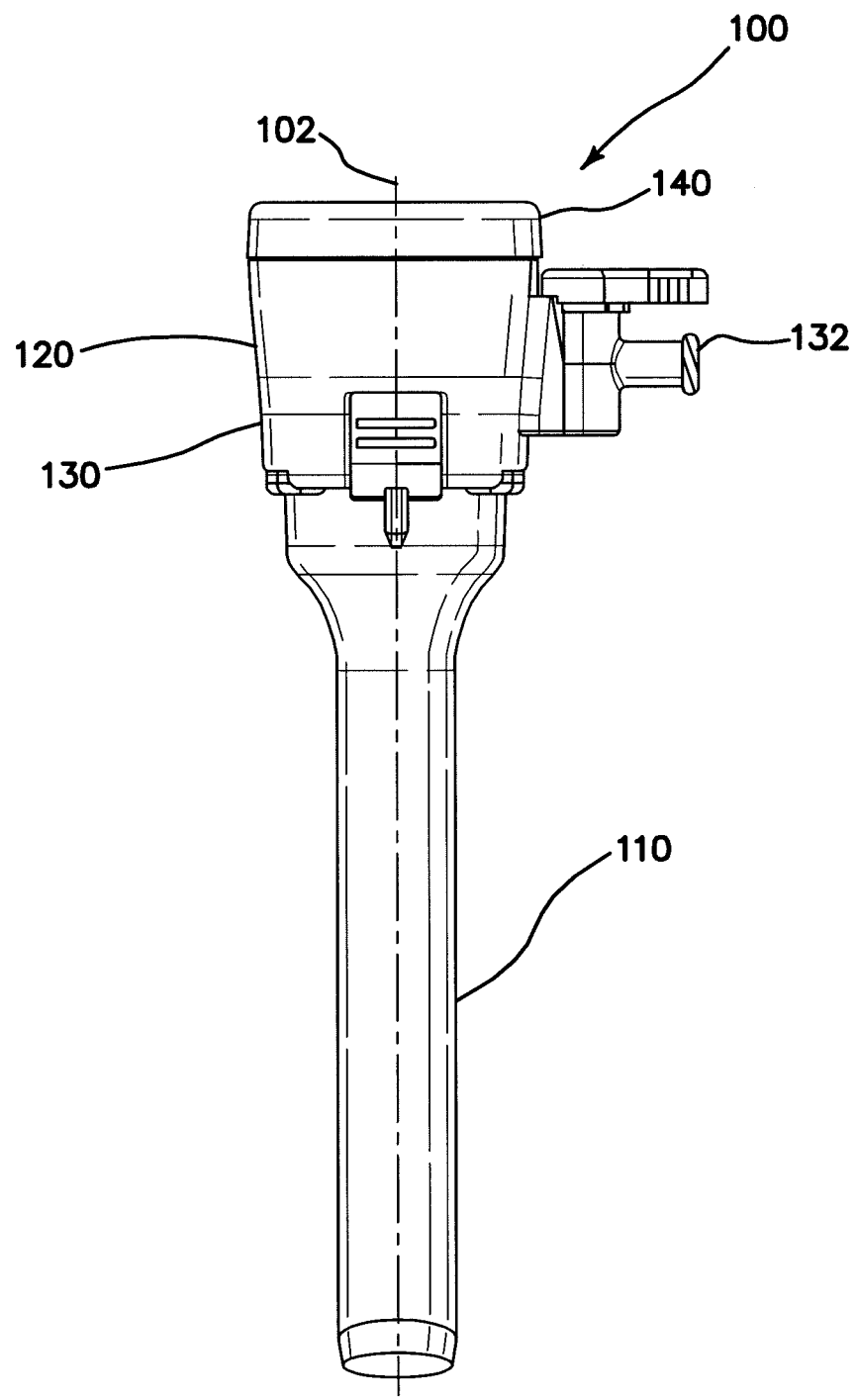
FIG. 1A is a side view of a surgical access device comprising an embodiment of an instrument seal.

FIG. 1A is a side view of a surgical access device 100, embodied as a trocar, comprising a proximal end, a distal end, and a longitudinal axis. A tubular cannula 110 comprising a longitudinal lumen is disposed at the distal end and is coupled to a seal assembly 120 at the proximal end. An instrument access channel 102 extends through the cannula 110 and seal assembly along the longitudinal axis in the illustrated embodiment. In the illustrated embodiment, the cannula 110 and seal assembly 120 are releasably coupled. In other embodiments, the cannula 110 and seal assembly 120 are integrated. An O-ring captured at the proximal end of the cannula 110 provides a fluid-tight seal between the cannula 110 and the seal assembly 120 in the illustrated embodiment. Embodiments of the cannula 110 are rigid or flexible.

Figure 1B:
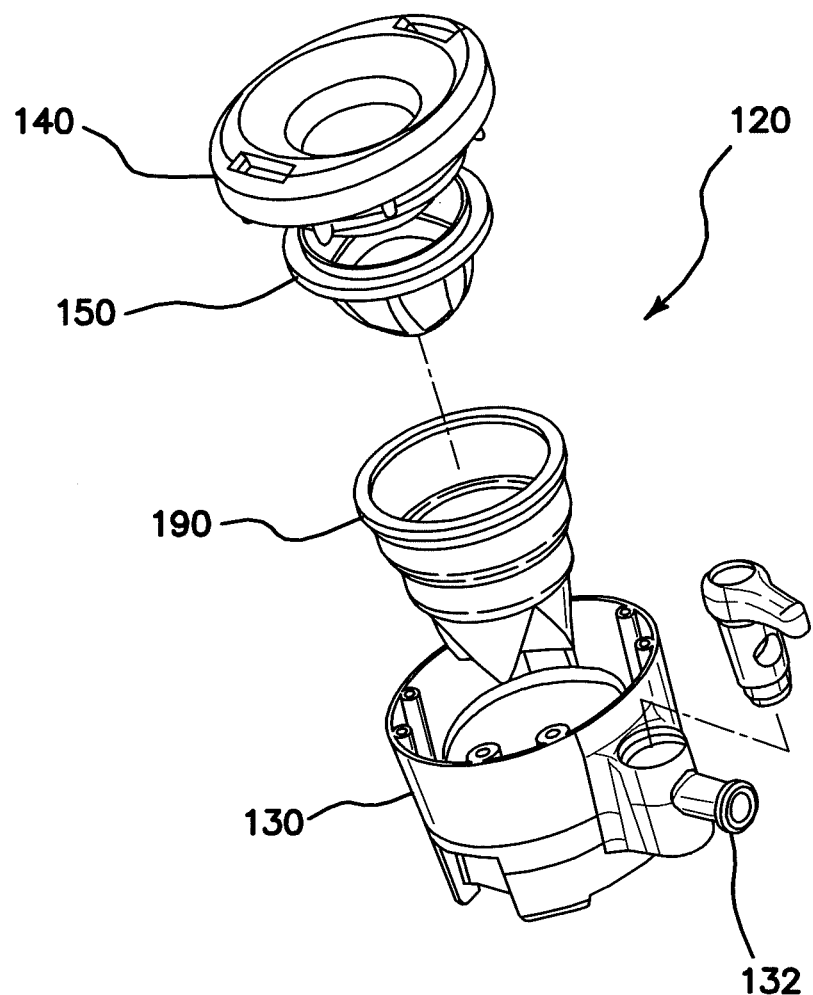
FIG. 1B is an exploded perspective view and FIG. 1C is a cross-sectional view of a seal assembly of the access device illustrated in FIG. 1A.
Figure 1C:
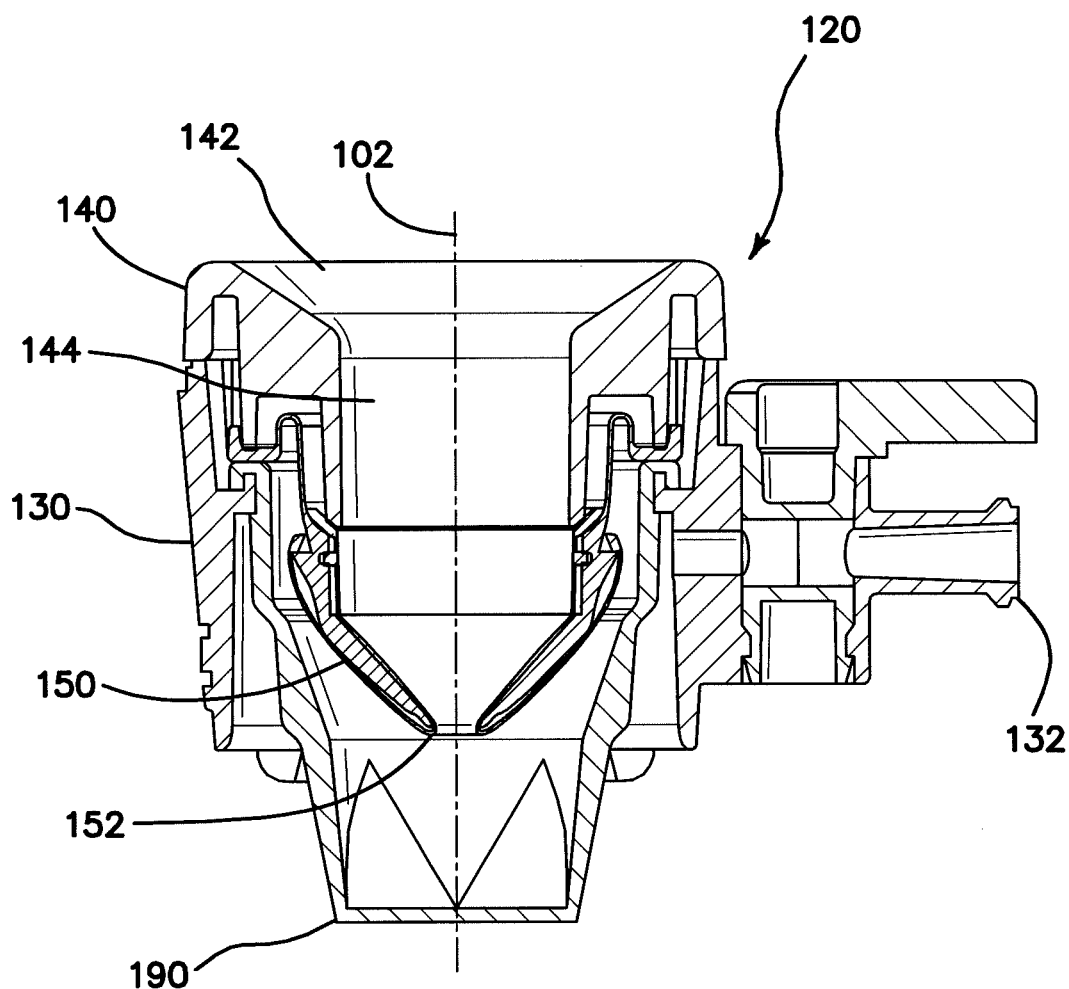

FIG. 1B is an exploded perspective view and FIG. 1C is a cross-sectional view of the seal assembly 120. The seal assembly 120 comprises a seal housing 130 comprising a fluid connector 132. In the illustrated embodiment, the fluid connector 132 comprises a radially extending Luer fitting and a stopcock. A cap or cover 140 closes a proximal end of the seal housing 130, securing within the housing 130 an instrument seal 150 and a zero seal 190.

In the illustrated embodiment, the cap 140 comprises a funneled entry 142 at a proximal end thereof, and an alignment channel 144 distal of the funneled entry 142. The funneled entry 142 guides instruments into the access channel 102, while the alignment channel 144 generally aligns an inserted instrument longitudinally with the access channel 102. Aligning the instrument with the access channel reduces instrument contact with off-axis portions of the device 100 or components thereof, thereby reducing damage thereto. The cap 140 is secured to the proximal end of the housing 130 using any suitable method, for example, mechanically (e.g., screw threads, clips, bayonet mounts, screws, latches, ratchets, pins, lock rings, flanges and grooves, splines), adhesively (e.g., glue, epoxy, urethane, cyanoacrylate, pressure sensitive adhesive, polyvinyl alcohol adhesive, butadiene-styrene adhesive), welding (e.g., thermal, solvent, electron beam, laser, ultrasonic), magnetically, and the like. In some embodiments, the cap 140 is secured to the housing 130 by a combination of methods.

The cannula 110, housing 130, and cap 140 independently comprise suitable biologically compatible materials or combinations thereof, for example, metal, stainless steel, aluminum, nickel-titanium alloy, polymer resin, polycarbonate, polyester, polyamide (Nylon®, Delrin®), aramid (Kevlar®), polyimide, polyether block amide (PEBAX®), polyolefin, polyethylene (Spectra®), polypropylene, fluorinated polymers, epoxy, polystyrene, polyvinyl chloride, polyvinylidene chloride, polycarbonate, polyvinyl chloride (PVC), polysulfone, polyetheretherketone (PEEK), polyepoxide, polyacrylate, polyether, acrylonitrile-butadiene-styrene (ABS), rubber, synthetic rubber, polyisoprene, silicone, ethylene propylene diene monomer (EPDM), ethylene-propylene copolymer (EP rubber), polybutadiene, polyurethane, styrene-butadiene, ethylene vinyl acetate (EVA), polychloroprene (Neoprene®), perfluorelastomer (Kalrez®), thermoplastic elastomer (HYTREL®, PELLETHANE®, KRATON®), glass, ceramic, carbon fiber, and the like. Some embodiments of suitable materials comprise copolymers, mixtures, blends, and/or alloys. Some embodiments of suitable materials comprise a composite, for example, a fiber reinforced polymer. Those skilled in the art will understand that different portions of a component comprise different materials in some embodiments.

The zero seal 190 comprises a generally funnel-shaped duckbill valve or double duckbill valve in the illustrated embodiment. The duckbill valve seals in the absence of an instrument extending therethrough, thereby preventing gas flow through the access channel 102 in the absence of an instrument and loss of pneumoperitoneum. In other embodiments, the zero seal 190 comprises a different type of valve, for example, a flap valve. Some embodiments of the access device 100 do not comprise a zero seal.

Embodiments of the zero seal 190 comprise one or more suitable materials. For example, some embodiments of the duckbill valve comprise an elastomeric material, for example, at least one of polymer resin, rubber, synthetic rubber, polyisoprene, silicone, ethylene propylene diene monomer (EPDM), ethylene-propylene copolymer (EP rubber), polybutadiene, polyurethane, styrene-butadiene, ethylene vinyl acetate (EVA), polychloroprene (Neoprene®), perfluorelastomer (Kalrez®), thermoplastic elastomer (HYTREL®, PELLETHANE®, KRATON®), as well as blends, mixtures, copolymers, and/or composites thereof. In some embodiments, the duckbill valve comprises polyisoprene.

Figure 1D:
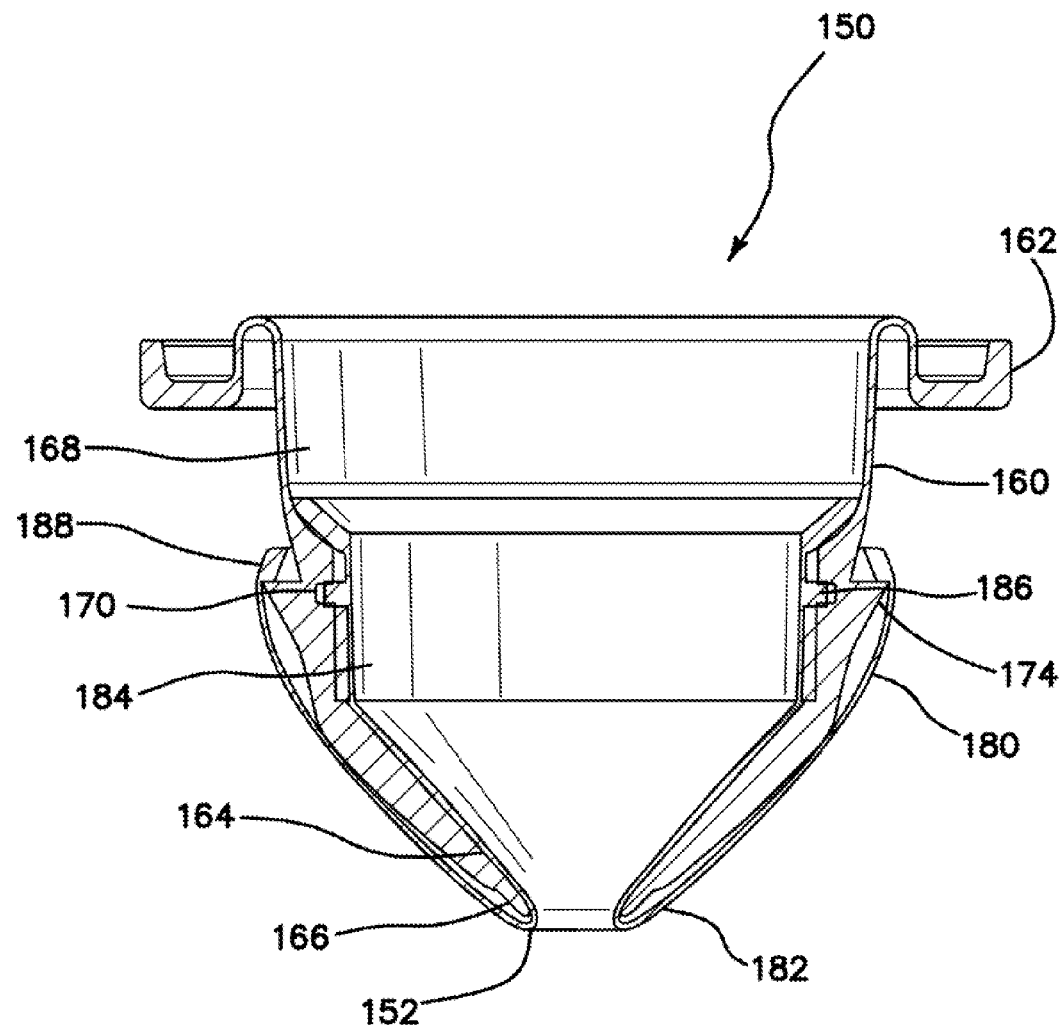
FIG. 1D is a cross section of the instrument seal illustrated in FIGS. 1B and 1C.

As best seen in FIG. 1D, which is a cross section of the instrument seal 150, the instrument seal 150 comprises a compression element 160 and an instrument contact element 180. The instrument seal 150 is generally funnel-shaped with an orifice 152 disposed at a distal end thereof. The funnel shape of the instrument seal 150 creates a funnel entry for instruments inserted through the access channel 102, with which the orifice 152 is aligned.

The compression element 160 comprises a proximal flange 162 extending radially from the housing 130 towards the longitudinal axis of the trocar 100. A distal region 164 of the compression element converges frustoconically, terminating in an opening 166. The illustrated embodiment of the flange 162 comprises a convolution or bellows that furnishes the distal end 164 with translational and rotational degrees of freedom, or "float", which accommodates lateral, longitudinal, and/or angular movements of an instrument extending through the opening 166, while maintaining a seal with the instrument. The illustrated embodiment of the compression element 160 has a general form resembling a septum seal, and as such, is also referred to herein as a septum seal, although the compression element 160 does not actually function as a septum seal.

Figure 1E:
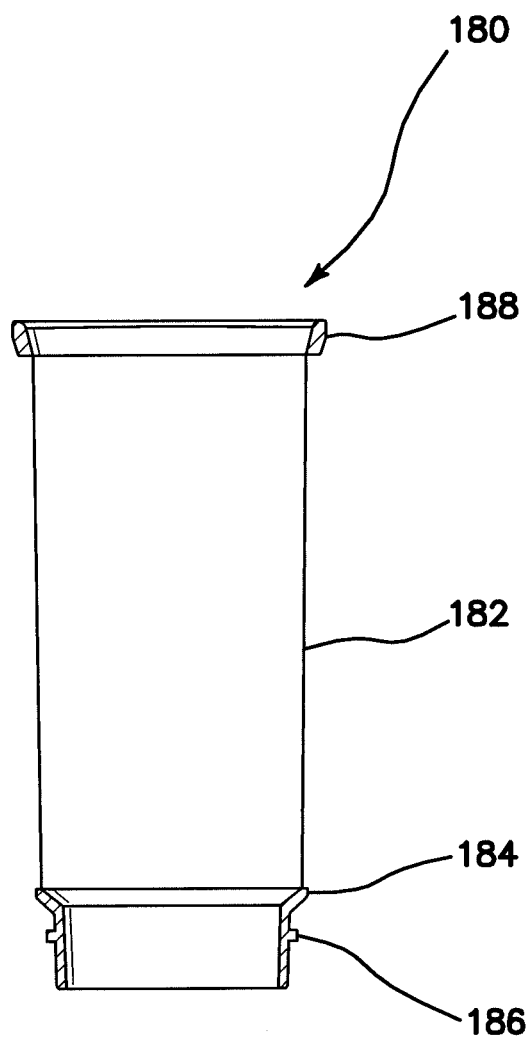
FIG. 1E is a cross section of an instrument contact element of the instrument seal of FIG. 1D in an unconstrained state.
Figure 1F:
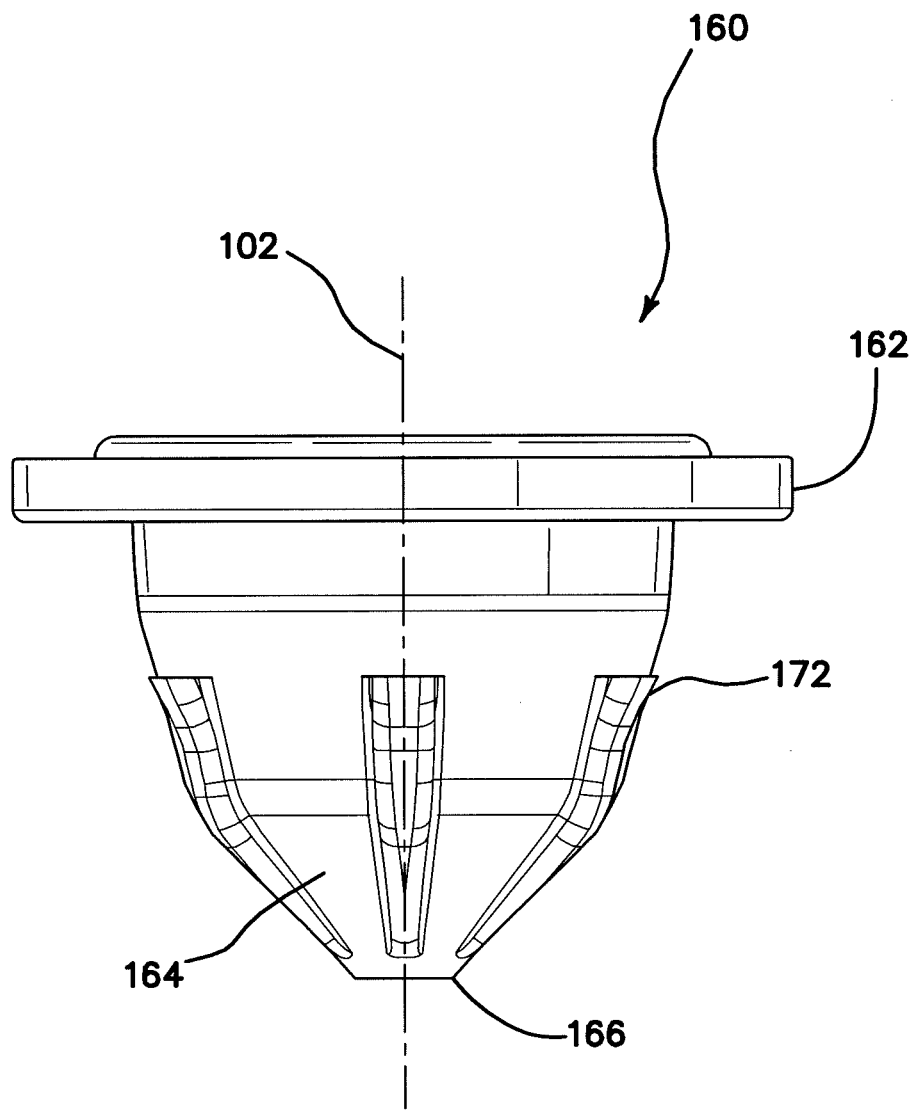
FIG. 1F is a side view of a compression element of the instrument seal of FIG. 1D.

FIG. 1E, which illustrates a cross section of the instrument contact element 180 in an unconstrained or relaxed state, the instrument contact element 180 comprises a tubular sheath, sleeve, or membrane 182 comprising a first end and a second end. In the illustrated embodiment, the first end of the membrane 182 is coupled to a first ring 184. As shown in FIG. 1D, the first ring 184 is disposed on an inner wall 168 of the compression element, for example, at or near the proximal end of the distal region 164 of the compression element. In the illustrated embodiment, an outwardly extending flange 186 on the first ring engages a groove 170 on the inner wall 168 of the compression element, thereby coupling the first ring 184 thereto. A second ring 188 is coupled to the second end of the membrane 182. The second ring 188 is disposed on an outer wall 174 of the compression element, and in the illustrated embodiment, engages proximal ends of a plurality of longitudinal ribs 172 disposed on the outer wall 174 of the compression element, which are best seen in FIG. 1F, a side view of the compression element 160. In some embodiments, the ribs 172 also reinforce the compression element 160, thereby reducing or preventing inversion thereof, for example, on withdrawing an instrument. In some embodiments, the second ring 188 is secured in another way, for example, using a flange and/or a groove. In some embodiments, the second ring 188 engages the first ring 184 through the compression element 160. In some embodiments, at least one of the first ring 184 and the second ring 188 is adhered and/or welded to the compression element 160. Because the instrument contact element 180 is disposed on the compression element 160 distal of the flange 162, the instrument contact element 180 moves in concert with distal portion 164 and opening 166 of the compression element. Consequently, the orifice 152 of the instrument seal is always aligned with the opening 166 of the compression element.

In the illustrated embodiment, the tubular membrane 182 extends through the first ring 184 and through the opening 166 in the compression element. The membrane 182 together with the opening 166, defines the orifice 152 in the instrument seal. The membrane 182 is doubled- or folded-back through the opening 166, thereby wrapping the opening 166 and distal region 164 of the compression element therewith, and protecting the opening 166 and distal region 164 from damage. As best seen in FIG. 1E, in an unconstrained state, the tubular membrane 182 is generally cylindrical. In the illustrated embodiment, a diameter of the tubular membrane 182 is at least as large as a diameter of a largest instrument for which the access device 100 is designed to accommodate. The diameter of the tubular membrane 182 is larger than a diameter of the opening 166 in the compression element. Consequently, the distal portion 164 of the compression element compresses the portion of the membrane 182 that passes through the opening 166, thereby generating a plurality of folds, pleats, gathers, or wrinkles therein. The folds or pleats in the membrane 182 around the orifice 152 tend to direct a tip of an inserted instrument longitudinally towards the orifice 152.

Because the diameter of the tubular membrane 182 is at least as large as a diameter of the largest instruments, inserted instruments do not stretch the diameter of the tubular membrane 182. Because the membrane 182 itself is not under tension even when the largest instrument is inserted therein, the membrane 182 does not compress the instrument, thereby reducing drag and friction therebetween. Instead of stretching the membrane 182, the instrument reduces and/or eliminates the fold or pleats when inserted. Durability is also improved by not stretching the membrane 182.

In the illustrated embodiment, the membrane 182 completely covers the opening 166. Consequently, an instrument inserted through the orifice contacts only the membrane 182 and does not directly contact the opening 166 or the distal portion 164 of the compression element. In other words, the membrane 182 spaces or isolates the instrument from the opening 166 or the distal portion 164 and the compression element in the illustrated embodiment.

In the illustrated embodiment, the membrane 182 is substantially taut or under tension between the first ring 184 and the second ring 188, acting as a trampoline, deflecting a tip of an instrument in contact therewith away from the underlying compression element 160, thereby preventing or reducing damage thereto. In other embodiments, the membrane 182 is not under tension. A looser membrane 182 generally accommodates more movement and/or deformation of the compression element 160 than a tighter membrane 182. In some embodiments, however, a looser membrane 182 transmits rather than deflects force from an incident instrument tip to the underlying compression element 160. In some cases, the transmitted force is sufficient to damage or puncture the compression element 160, sometimes without puncturing the membrane 182 itself.

In the illustrated embodiment, the membrane 182 is a closed tube. In other embodiments, the membrane 182 comprises a tube with abutting or overlapping longitudinal edges. The illustrated embodiment of the membrane 182 in an unconstrained state is generally cylindrical. In other embodiments, the membrane 182 has another shape, for example, frustoconical, hourglass shaped, barrel shaped, or abutting cylinders with different diameters. In other embodiments, the membrane 182 has a different cross-sectional shape, for example, elliptical, oval, polygonal, and the like.

Some embodiments of the membrane 182 comprise at least one slit, slot, or opening extending from proximal of the orifice 152 to distal of the orifice 152, for example, from the first end of the membrane 182 to the second end of the membrane 182. Some embodiments of the at least one slit, slot, or opening are generally longitudinal, while other embodiments are angled or at a bias with respect to a longitudinal axis of the membrane 182. In some embodiments, the at least one slit, slot, or opening generates one or more overlapping layers of the membrane 182 at the orifice, thereby reducing or eliminating folds and/or pleats in the membrane 182 at the orifice 152.

The distal region 164 of the compression element comprises an elastomeric material selected to compress the instrument contact element 180 against an instrument extending through the orifice 152, thereby forming a seal therewith. In some embodiments, the entire compression element 160 comprises an elastomeric material. Some embodiments of the elastomeric material have an elongation of at least about 500%, at least about 600%, or at least about 700%. A material with a higher elongation generally seals with larger diameter instruments for a given compression element 160. Suitable elastomeric materials include polymer resin, rubber, synthetic rubber, polyisoprene, silicone, ethylene propylene diene monomer (EPDM), ethylene-propylene copolymer (EP rubber), polybutadiene, polyurethane, styrene-butadiene, ethylene vinyl acetate (EVA), polychloroprene (Neoprene®), perfluoroelastomer (Kalrez®), thermoplastic elastomer (HYTREL®, PELLETHANE®, KRATON®), as well as blends, mixtures, copolymers, and/or composites thereof. In some embodiments, the compression element 160 comprises polyisoprene. Because the instrument does not directly contact the compression element 160 in some embodiments, coefficient of friction, strength, tear resistance, puncture resistance, and/or abrasion resistance of the material is not as important in these embodiments.

The membrane 182 comprises a material selected to provide at least one of puncture resistance, tear resistance, tensile strength, durability, abrasion resistance, good sealing characteristics, flexibility, and low friction. Embodiments of the membrane 182 are substantially non-distensible under the working conditions of the access device 100. Examples of suitable non-distensible materials include polymer resin, polymer resin, polycarbonate, polyester, polyamide (Nylon®, Delrin®), aramid (Kevlar®), polyimide, polyether block amide (PEBAX®), polyolefin, polyethylene (Spectra®), polypropylene, fluorinated polymers, epoxy, polystyrene, polyvinyl chloride, polyvinylidene chloride, polycarbonate, polyvinyl chloride (PVC), polysulfone, polyetheretherketone (PEEK), polyepoxide, polyacrylate, polyether, acrylonitrile-butadiene-styrene (ABS), as well as blends, mixtures, copolymers, and/or composites thereof. Some embodiments of the membrane 182 comprise a polyolefin.

Other embodiments of the membrane 182 are elastomeric or distensible, for example, comprising at least one of polymer resin, rubber, synthetic rubber, polyisoprene, silicone, ethylene propylene diene monomer (EPDM), ethylene-propylene copolymer (EP rubber), polybutadiene, polyurethane, styrene-butadiene, ethylene vinyl acetate (EVA), polychloroprene (Neoprene®), perfluoroelastomer (Kalrez®), thermoplastic elastomer (HYTREL®, PELLETHANE®, KRATON®), as well as blends, mixtures, copolymers, and/or composites thereof. Embodiments of membranes 182 comprising elastomeric or distensible materials provide improved sealing to the instrument and/or itself, while increasing friction or drag, which increases the likelihood of puncturing the membrane 182 and/or decreases the durability thereof.

Some embodiments of the membrane 182 comprise a composite, for example, comprising a low friction surface layer or film, and a high strength layer or film. Some embodiments comprise reinforcing fibers, which improve strength. In some embodiments, the membrane 182 is anisotropic, for example, with high strength in a longitudinal direction and high foldablity in a transverse direction.

Some embodiments of the membrane 182 comprise a coating comprising at least one of an oil, silicone oil, thin gel film, and lubricious coating, which reduces friction with an instrument in contact therewith. In some embodiments, the coating also improves sealing with the instrument, as well as self-sealing of the folds or pleats in the membrane 182. In particular, the membrane 182 comprises more and/or larger folds or pleats in the presence of smaller instruments or no instrument at all.

Some embodiments of the membrane 182 comprise a textured surface, which reduces friction, for example, dots, bumps, stripes, ridges, and the like. The texture is patterned or random.

Although a low friction for instrument movement in the instrument seal 150 is desirable, some friction is desirable in some embodiments. For example, sufficient friction to maintain the position of an instrument in the instrument seal 150 relieves a user from holding the instrument in place to prevent undesired movement.

Embodiments of the membrane 182 are not greater than about 250 µm (about 10 mil), not greater than about 125 µm (about 5 mil), not greater than about 25 µm (about 1 mil), not greater than about 12 µm (about 0.5 mil), not greater than about 5 µm (about 0.2 mil), or not greater than about 2 µm (about 0.1 mil). Those skilled in the art will understand that the thickness of a membrane 182 will depend on the material and a balancing of desired properties of the membrane 182. For example, a thicker membrane generally has higher strength, tear resistance, puncture resistance, durability, and abrasion resistance. A thinner membrane generally conforms better to an instrument and to itself, and accordingly, seals better.

One criterion for quantifying the seal between the instrument seal 150 and an instrument is a leak rate. While a zero leak rate may be desirable in some cases, insufflators are capable of delivering insufflation gas at high rates, for example, up to about 30 L/min or up to about 40 L/min. Such an insufflator is capable of compensating for leaks from up to four or five access devices, each with an instrument seal exhibiting a leak rate of up to about 400 mL/min, up to about 500 mL/min, up to about 1,000 mL/min, or up to about 1,500 mL/min at about 2 kPa (about 15 Torr, 8 inches of water). Leak rates are for instrument seals 150 with and/or without an instrument inserted therein.

Embodiments of the access device 100 accommodate instruments of different sizes. For example, embodiments of the access device 100 include trocars that accommodate instrument with diameters of up to about 5 mm, up to about 8 mm, up to about 11 mm, up to about 12 mm, or up to about 15 mm. Some embodiments seal with instruments with diameters of from about 4.5 mm to about 15.4 mm. Some embodiments of the access device 100 accommodate a surgeon's hand. Some embodiments of the access device 100 comprise a plurality of instrument seals 150, thereby permitting the introduction of a plurality of instruments through a single device.

Figure 2:
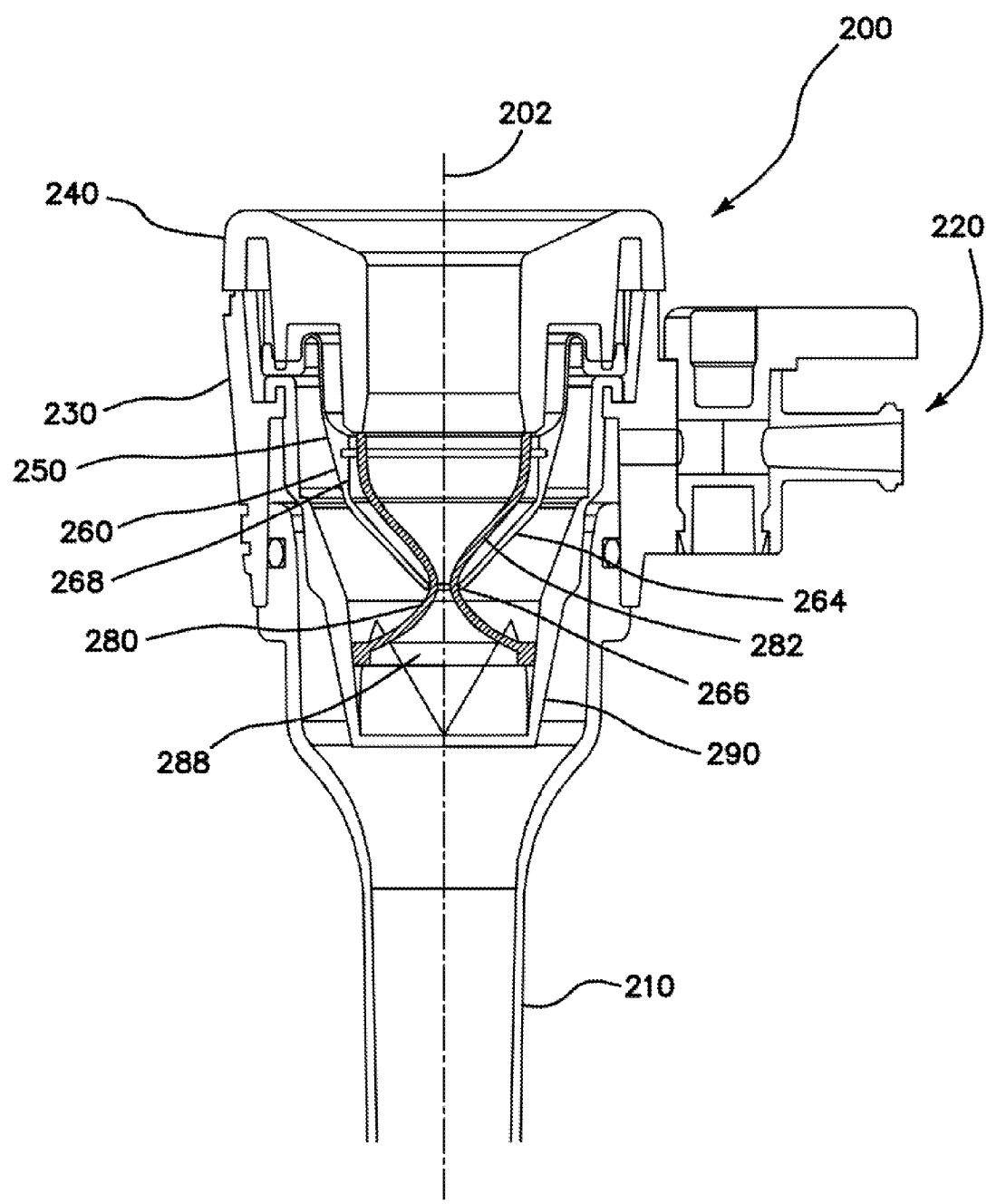
FIG. 2 is a cross section of an access device comprising another embodiment of an instrument seal.

FIG. 2 is a cross section of an embodiment of an access device 200 similar to the embodiment illustrated in FIGS. 1A-1F. The access device 200, embodied as a trocar, comprises a cannula 210 and a seal assembly 220. The seal assembly 220 comprises a seal housing 230 and a cap 240, which capture an instrument seal 250 and a zero seal 290. The instrument seal 250 comprises a compression element 260 and an instrument contact element 280. In the illustrated embodiment, the instrument contact element 280 comprises a membrane 282. A first end of the membrane 282 is coupled to an inner wall 268 of the compression element. The membrane 282 extends through an opening 266 that terminates a distal portion 264 of the compression element. A second end of the membrane 282, disposed distal of the opening 266, is coupled to a ring 288. An inner diameter of the ring 288 is about the same as a diameter of the membrane 282.

The ring 288 has a diameter greater than the diameter of the opening 266, thereby preventing the second end of the membrane 282 from passing therethrough. Some embodiments of the ring 288 comprise a disc weight, which tensions the membrane 282 when the access device 200 is in a generally upright position as shown in FIG. 2. Some embodiments comprise a tensioning element (not illustrated) that urges the ring 288 distally, thereby maintaining the membrane 282 under tension when the access device 200 is in other positions. The tensioning element itself is under tension, under compression, or comprises at least one component under tension and at least one component under compression. Embodiments of the tensioning element comprise, for example, at least one of a spring, an elastic band, a resilient member, a balloon, and the like. Some embodiments comprise a stop (not illustrated) that limits proximal movement of the ring 288. Embodiments in which the ring 288 is free to move within the seal housing 230 accommodate greater off-axis and/or angular positioning of an instrument.

In the illustrated embodiment, the membrane 282 has a generally hourglass shape, with the opening 266 of the compression element defining a waist portion of the hourglass shape. The waist portion of the hour glass defines an orifice of the instrument seal. The ring 288 also keeps the second end of the membrane 282 open, thereby maintaining the hourglass shape of the membrane 282. The hourglass shape of the membrane 282 provides a funnel entry to the orifice for both proximal and distal approaches thereto along an access channel 202 of the access device.

Figure 3A:
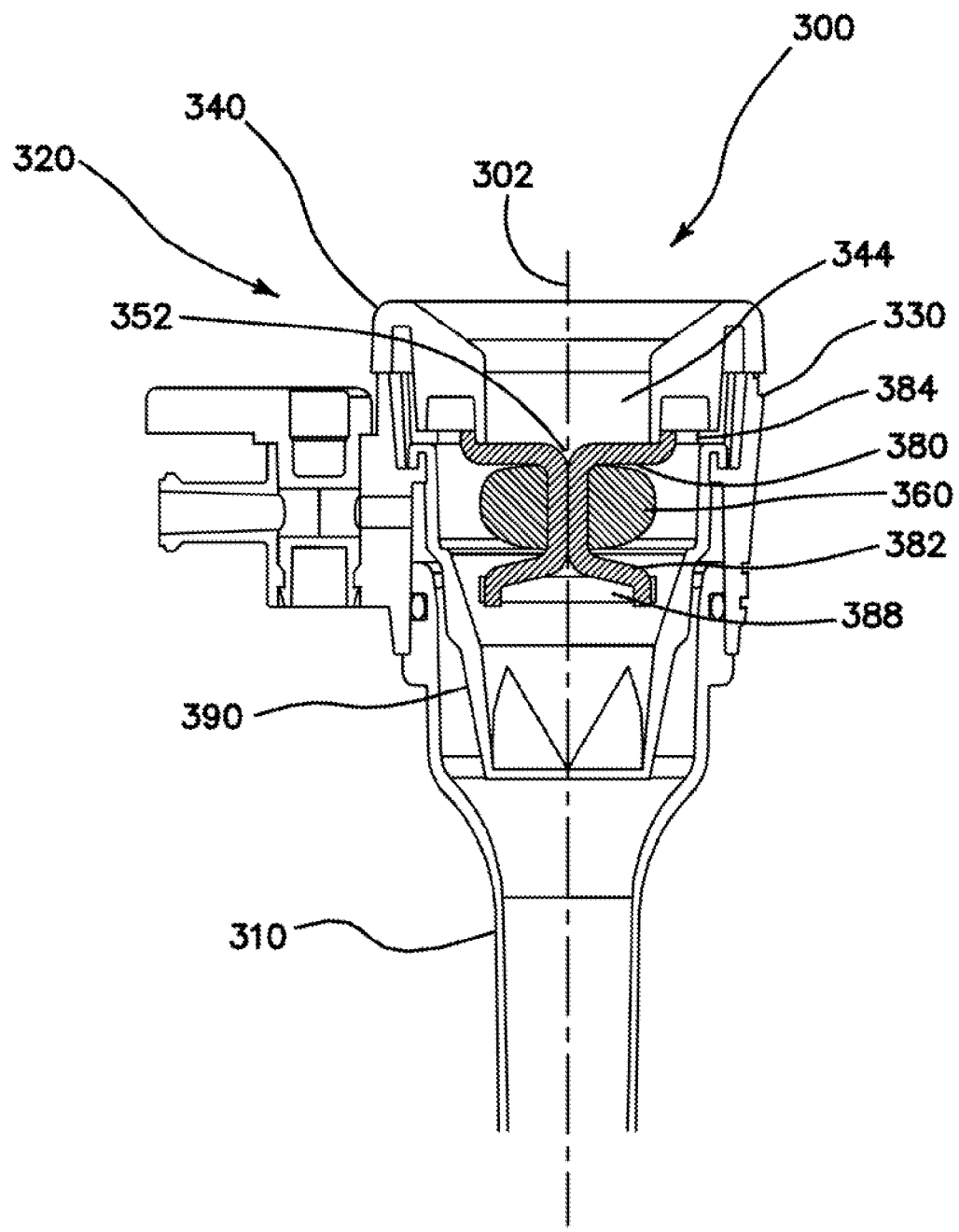
FIG. 3A is a cross section of an access device comprising another embodiment of an instrument seal.
Figure 3B:
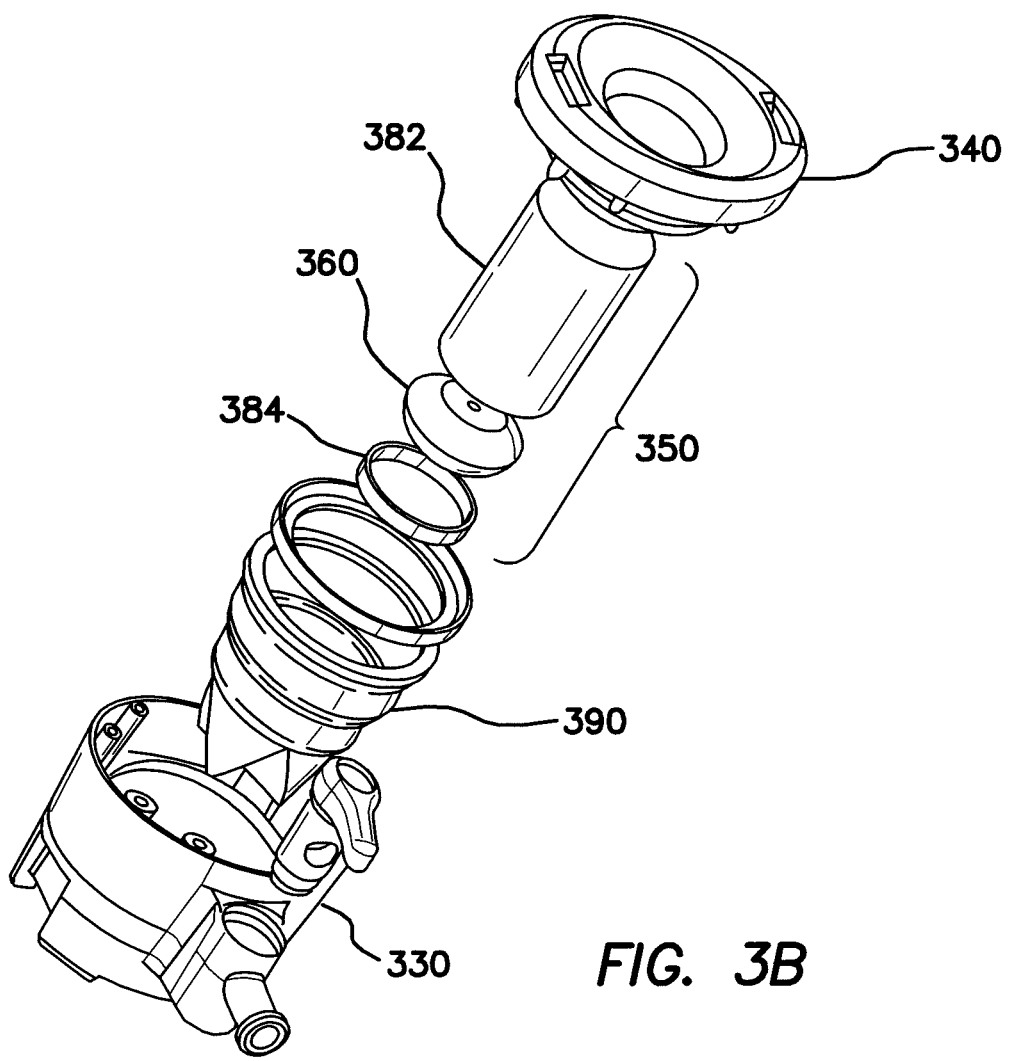
FIG. 3B is an exploded view of a seal assembly of the access device of FIG. 3A.

FIG. 3A is a cross section of another embodiment of an access device 300, which is similar to the embodiments described above. The access device 300 comprises a cannula 310 and a seal assembly 320. FIG. 3B is an exploded view of the seal assembly 320, which comprises a seal housing 330, a cap 340, an instrument seal 350, and a zero seal 390. The instrument seal 350 comprises a compression element 360 and an instrument contact element 380.

In the illustrated embodiment, the compression element 360 comprises a gel disc comprising a generally circular opening 366 extending longitudinally through the center thereof as best seen in FIG. 3C. The opening 366 is aligned with the access channel 302. In some embodiments, the opening 366 has a small diameter, for example, formed by passing a needle through the compression element 360.

Embodiments of the compression element 360 comprise a gel material. Embodiments of suitable gel materials are biocompatible and exhibit high elongations, low durometer, and high tear strengths. Embodiments of the gel material comprise a thermoplastic elastomeric diblock and/or a triblock copolymer, and an oil. Examples of suitable diblock copolymers include styrene-ethylene/butylene (S-E/B), and the like. Examples of suitable triblock copolymers include styrene-ethylene/butylene-styrene (S-E/B-S), styrene-isoprene-styrene, (S-I-S), styrene-butadiene-styrene (S-B-S), styrene-ethylene/propylene-styrene (S-E/P-S), and the like. Examples of suitable diblock and triblock copolymers are commercially available as KRATON® (Kraton Polymers) and SEPTON® (Kuraray Co.). In some embodiments, the copolymer is a KRATON® triblock copolymer. Examples of suitable oils include mineral oil, vegetable oil, petroleum oil, silicone oil, and mixtures thereof. In some embodiments, the oil is mineral oil. Embodiments of the gel material comprise at least about 6:1, at least about 1:5, or at least about 1:10 KRATON® to mineral oil by weight. Embodiments of the gel material comprise up to about 1:15 KRATON® to mineral oil by weight.

Some embodiments of the gel material exhibit an ultimate elongation of at least about 1000 percent and a durometer less than about 5 Shore A, and are referred to ultragels. Some embodiments exhibit an ultimate elongation of at least about 1500 percent and a durometer less than about 200 Bloom. Some embodiments exhibit an ultimate elongation of at least about 3000 percent. Embodiments of gel and ultragel materials have a tacky or sticky surface. In some embodiments, the surface is treated to reduce the tackiness, for example, by powdering and/or skinning with a polymer film. In other embodiments, the surface is untreated because the instrument contact element 380 is disposed between the compression element 360 and an instrument extending through the opening 366, thereby preventing contact therebetween.

As discussed above, a higher elongation material seals with larger instruments. Consequently, embodiments of gel compression elements 360 with higher elongations are capable of sealing with instruments with a wider range of diameters than similar compression elements comprising lower elongation materials. Accordingly, in some embodiments, the orifice 352 has a zero or near-zero diameter in the absence of an instrument, while still able to seal larger instruments. In some of these embodiments, the leak rate of the instrument seal 350 without an instrument inserted therethrough is sufficiently low that an insufflator is capable of compensating for the leak, as discussed above. In some of these embodiments, the instrument seal 350 functions as a zero seal, and consequently, the zero seal 390 is optional.

Embodiments of gel materials also exhibit a low modulus. Otherwise similar compression elements, one comprising gel and the other comprising rubber, will exhibit very different correlations between instrument drag and instrument diameter. With the largest diameter instrument that the rubber compression element will accommodate inserted therein, the rubber is close to the elastic limit on the stress-strain curve where the modulus is high. In contrast, with the same diameter instrument inserted in the gel compression element, the gel is not close to the elastic limit. In this region of the stress-strain curve, the modulus is low. Consequently, differences in the force required to insert instruments of different diameters are smaller for the gel compression element compared with the rubber compression element, resulting in a more consistent instrument drag for the gel compression element.

The compression element 360 applies only compression in response to an instrument inserted in the opening 366 rather than any twisting or rotational forces. Accordingly, the high elongation materials, including gels and ultragels, also conform more effectively to out of round and non-round shapes, thereby improving sealing to instruments with such cross sections.

Some embodiments of the compression element 360 comprise a foamed soft elastomer with properties similar to the gel and/or ultragel materials discussed above, for example, foamed KRATON®, foamed MONOPRENE® (Poly-Med Inc.), and the like.

As discussed above, the instrument contact element 380 prevents contact between the compression element 360 and an instrument, thereby permitting the use of the soft and easily damaged materials discussed above.

The instrument contact element 380 comprises membrane 382 extending through the opening 366 in the compression element, with a first end proximal of the compression element 360 and a second end distal of the compression element 360. In the illustrated embodiment, the first end of the membrane 382 is coupled to a first ring 384 which is captured between the cap 340 and the seal housing 330, thereby securing the first end of the membrane 382. In other embodiments, the first end of the membrane 382 is secured in another way, for example, operatively coupled to a distal end of the alignment channel 344 of the cap. The second end of the membrane 382 is coupled to a second ring 388. An inner diameter of the second ring 388 is about the same as the diameter of the membrane 382 in the illustrated embodiment. Some embodiments of the second ring 388 comprise a disc weight, as discussed above. Also as discussed above, some embodiments of the instrument contact element 380 comprise an optional tensioning element and/or stop for the second ring 388. In other embodiments, the second end of the membrane 382 is operatively coupled to the seal housing 330, for example, through the second ring 388, and the first end floats.

The membrane 382 in the illustrated embodiment has a generally hourglass shape with the portion of the membrane 382 extending through the opening 366 in the compression element defining an orifice 352 in the instrument seal 350, which is aligned with the access channel 302. The first ring 384 and the second ring 388 of the instrument contact element capture the compression element 360 therebetween, thereby securing the compression element 360. Accordingly, the compression element 360 can float laterally in concert with lateral movements of instruments in the access channel 302, thereby tracking the instrument. As discussed above, the hourglass shape of the membrane 382 defines funnel entries for both inserting and withdrawing instruments into and from the orifice 352 of the instrument seal, respectively.

Interactions between embodiments of the instrument seal and various instruments are described with reference to the embodiment of the access device 300 illustrated in FIGS. 3A-3C, although those skilled in the art will understand that the discussion is also applicable to other embodiments described herein.

Figure 3D:
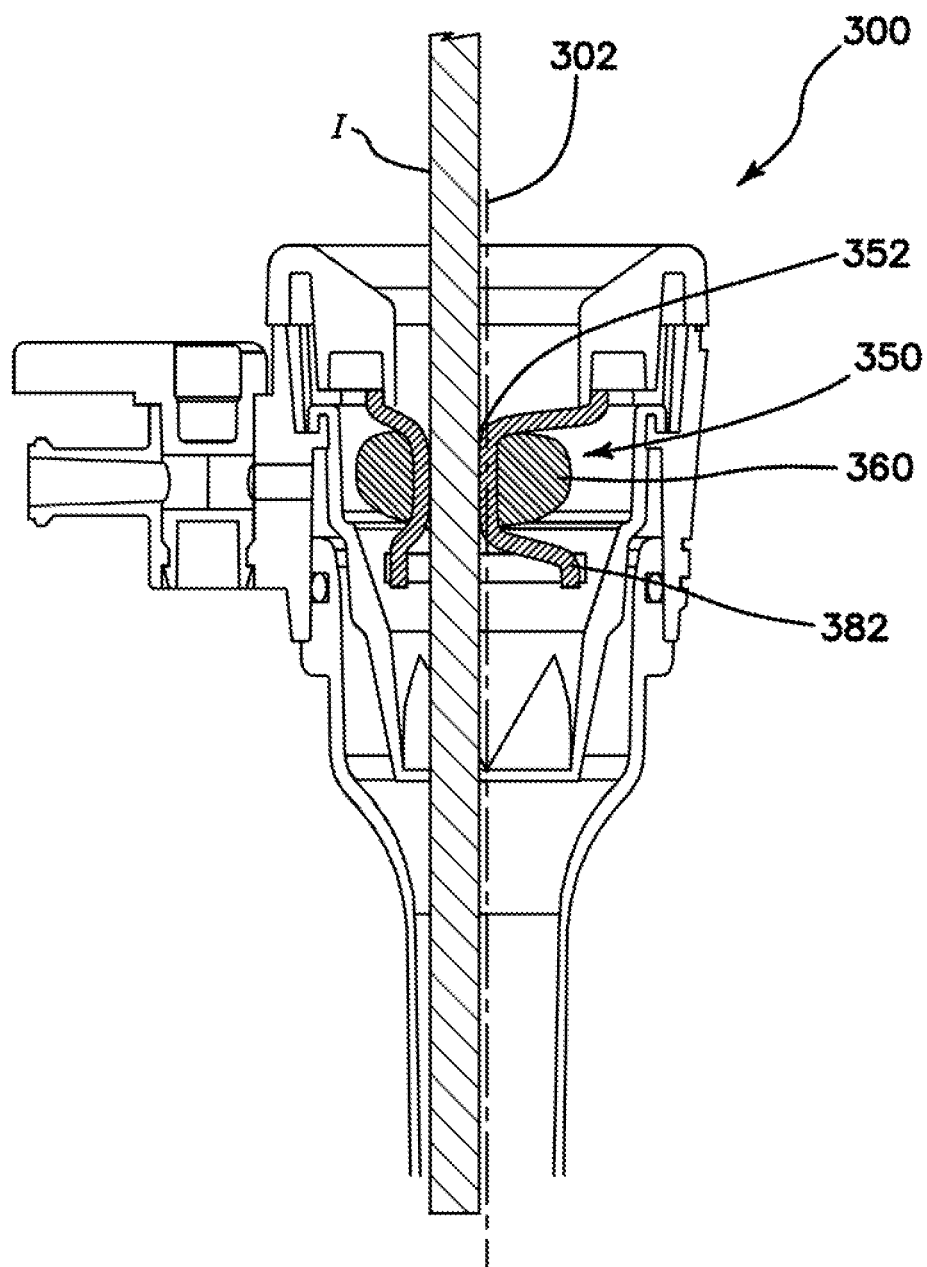
FIG. 3D is a cross-sectional view of the access device of FIG. 3A-3C with an instrument inserted therein.

FIG. 3D is a cross-sectional view of the access device 300 with an instrument I inserted off-axis into the access channel 302. In the illustrated embodiment, the axis of the instrument I is left of the access channel 302. The compression element 360 floats to the left, which shifts the orifice 352 of the instrument seal to the left while maintaining a seal with the instrument I. The orifice 352 of the instrument seal tracks lateral movements of instruments, thereby reducing the likelihood of "cat-eye" leaks in which a trailing edge of the orifice 352 loses contact with the instrument I. The amount of side-to-side motion that the instrument seal 350 will accommodate depends on factors including the distance between the first end of the membrane 382 and the sealing orifice 352, and the diameter of the membrane 382.

The illustrated embodiment of the access device 300 also exhibits lower hysteresis compared with a typical septum seal when moving the instrument I longitudinally in the instrument channel 302, that is inserting, withdrawing, or changing direction. Because a septum seal is typically flat or conical, advancing the instrument I followed by withdrawing tends to oil-can or pop the septum from a concave to a convex shape. The instrument drag perceived by the user on this change in direction is different from the uniform drag experienced during the insertion phase. On continued withdrawal of the instrument I, the septum remains in the convex configuration and the user again experiences a uniform drag. Changing direction again pops the septum back into the concave configuration, again, with a sudden change in drag. Consequently, the user experiences hysteresis in the drag on cyclical insertion and removal of the instrument I.

In the illustrated device 300, the sealing orifice 352 of the instrument seal is coupled to the seal housing 330. Therefore, changing direction from inserting to withdrawing the instrument I adds only the weight of the compression element 360 to the withdrawal force. Furthermore, the first ring 384 and the second ring 388 restrict axial or longitudinal movement of the compression element 360, thereby further reducing hysteresis. In some embodiments, axial movement of the compression element 360 is further restricted, for example, by disposing the compression element 360 in a conical support or other support structure. Consequently, the instrument seal 350 has comparatively predicable instrument-movement characteristics in which the surgeon experiences the same drag force and "feel" of the instrument I during insertion and removal. This consistency assures the surgeon that the instrument seal 350 is operating properly, reduces trocar cannula displacement, and reduces fatigue of the surgeon from manipulating instruments throughout the operation.

Figure 3E:
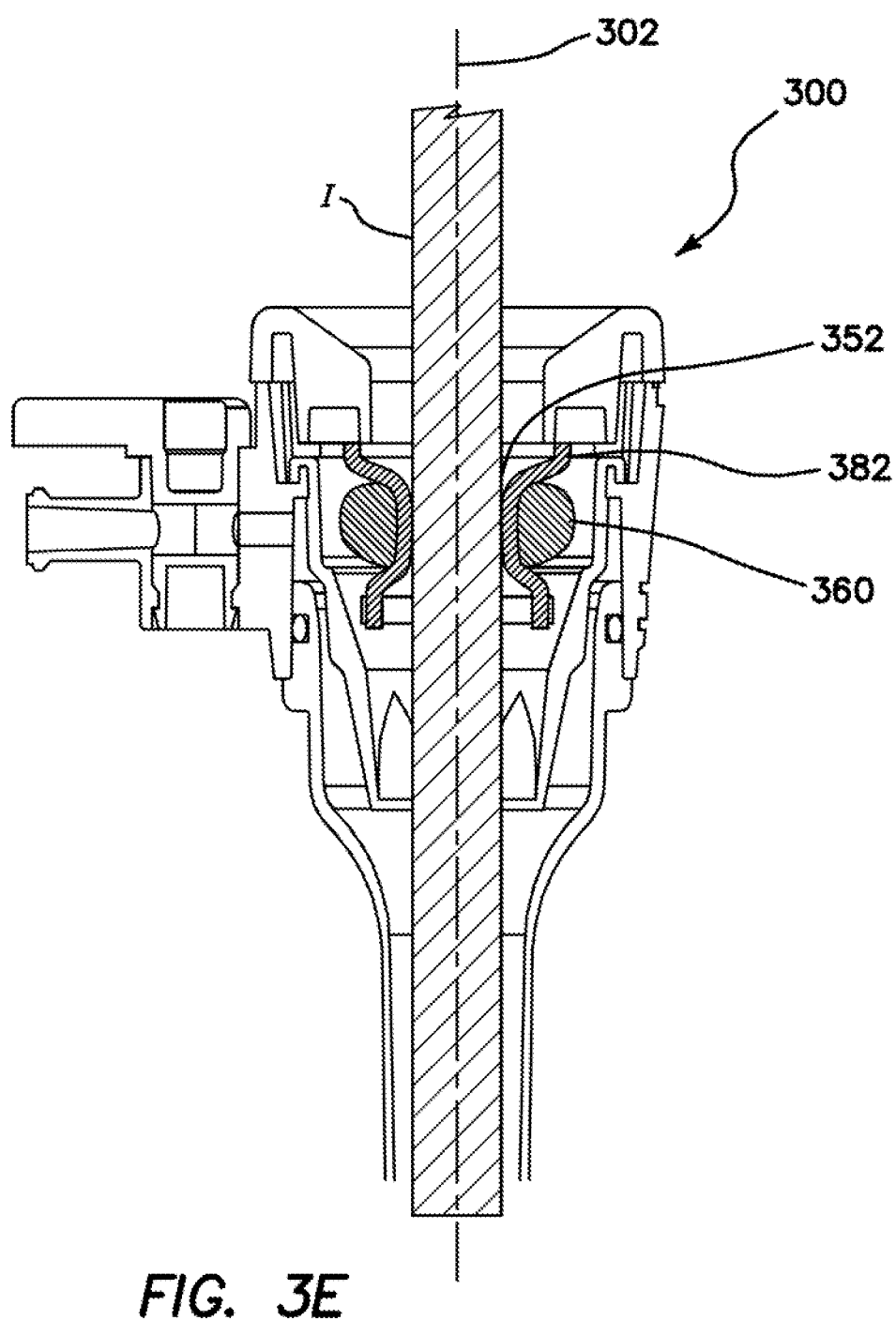
FIG. 3E is a cross-sectional view of the access device of FIG. 3A-3C with a larger instrument inserted therein.

FIG. 3E is a cross section of the access device 300 with a larger diameter instrument I inserted off-axis into the access channel 302. As with the embodiment illustrated in FIG. 3D, the compression element 360 shifts laterally to accommodate the off axis instrument I, as well as increasing the size of the opening 366, while maintaining the seal at the orifice 352. As discussed above, in embodiments comprising a compression element 360 with a lower modulus, a user will experience a more constant instrument drag with both the larger diameter instrument illustrated in FIG. 3E and the smaller diameter instrument illustrated in FIG. 3D.

Figure 3F:
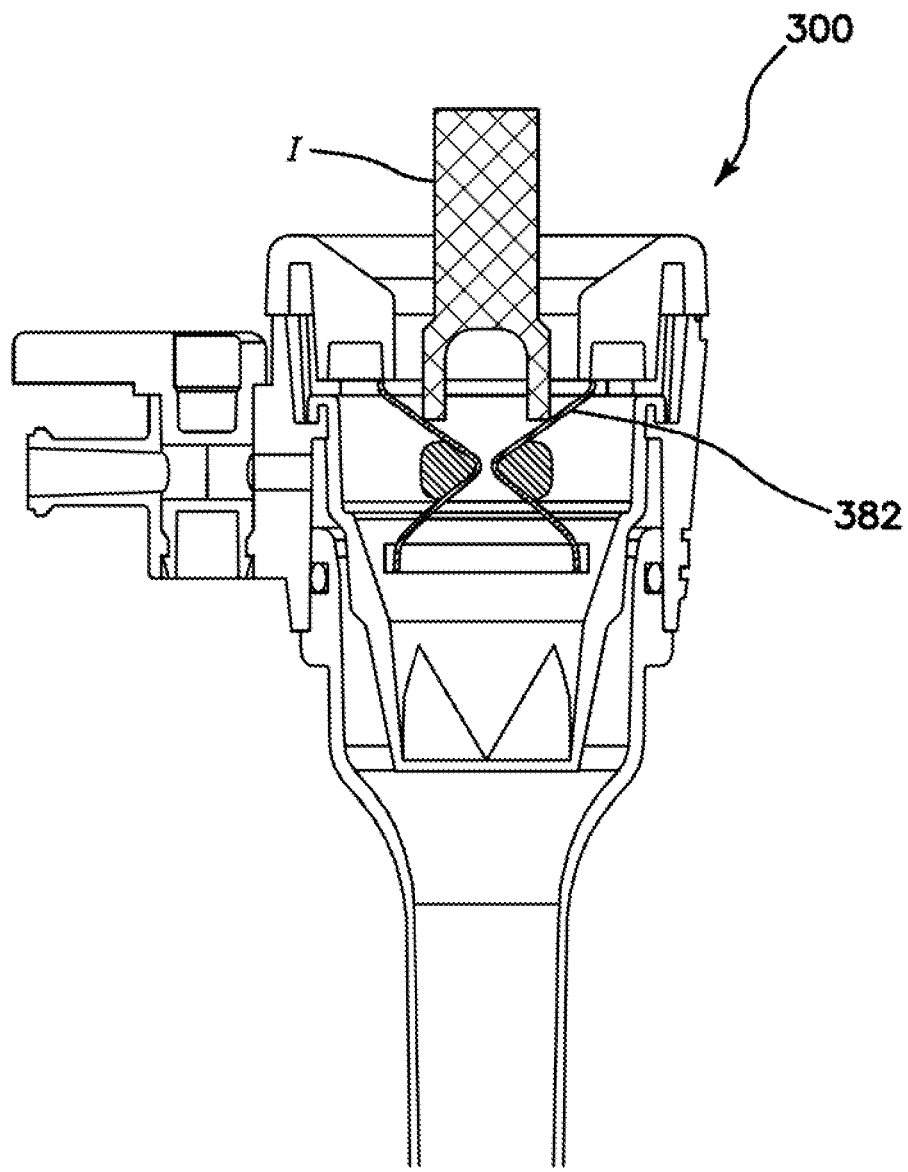
FIG. 3F is a cross-sectional view of the access device of FIG. 3A-3C with a fork-tipped instrument inserted therein.

FIG. 3F is a cross section of the access device 300 with an instrument I approaching the instrument seal 350. The illustrated instrument I comprises a forked, pointed tip, which is considered a difficult geometry with respect to potential damage. Such a geometry is found, for example, in some clip appliers. The hourglass shape of the membrane 382 creates a funnel or ramped entry to the orifice 352, thereby reducing the likelihood of damage thereto. The analogous orifice in a typical septum seal is typically the most vulnerable portion thereof. Contact between the tip and the membrane 382 also causes the instrument seal 350 to pendulate away from the tip, thereby further reducing potential damage.

Figure 3G:
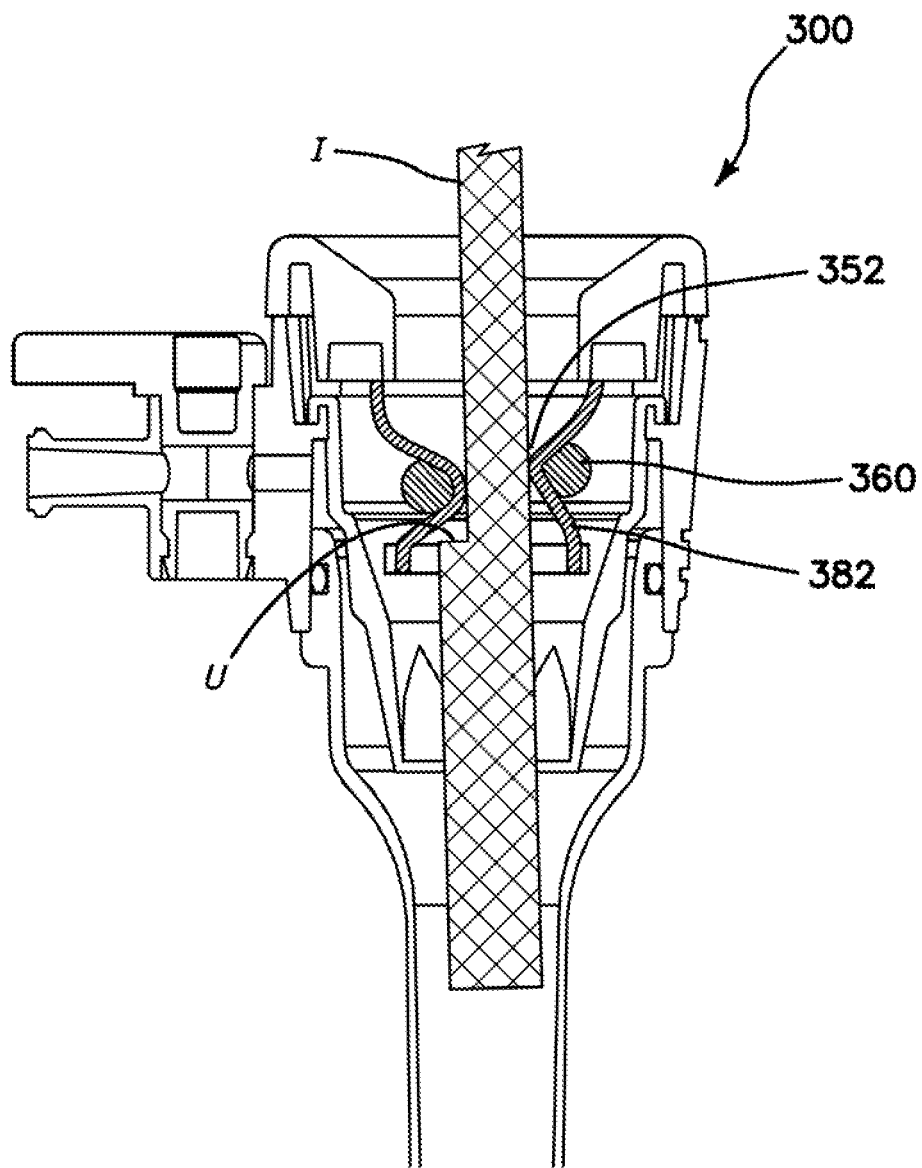
FIG. 3G is a cross-sectional view of the access device of FIG. 3A-3C with an instrument comprising an undercut inserted therein.

FIG. 3G is a cross section of the access device 300 with an instrument I comprising an undercut U in the instrument seal 350. Undercuts are another difficult geometry with respect to withdrawing the instrument from an instrument seal, and are found, for example, in endoscopic staplers. Again, the hourglass shape of the membrane 382 creates a funnel entry or exit to the orifice 352 for withdrawn instruments I, thereby reducing damage thereto. The smooth transition between the distal surface of the membrane 382 and the portion around the orifice 352 also reduces potential catches or snags. Furthermore, the compression element 360 tends to move laterally in response to features on the instrument, taking a path of least resistance, thereby reducing damage to the instrument seal 350.

Moreover, the reduced friction between the instrument I and the orifice, the strength of the membrane 382, and the isolation of the compression element 360 from the instrument I also contribute to the improved durability of the illustrated instrument seal 350 compared with a typical septum seal. Accordingly, the embodiment 100 illustrated in FIGS. 1A-1F in which the membrane 182 wraps the opening 166 in the compression element will also exhibit improved durability and reduced likelihood of damage from withdrawing instruments with difficult geometries, such as undercuts and protuberances.

Figure 4:
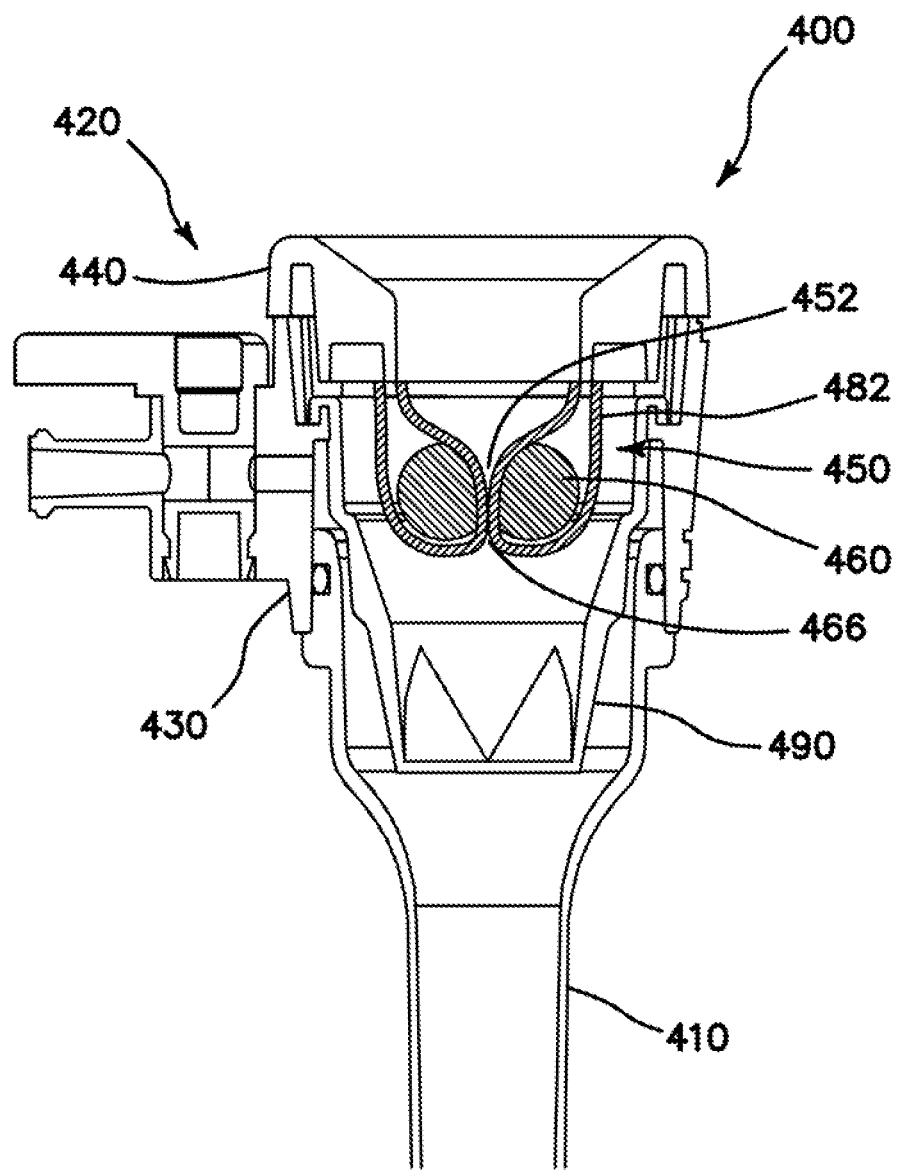
FIG. 4 is a cross section of an access device comprising another embodiment of an instrument seal.

FIG. 4 is a cross section of another embodiment of an access device 400 similar to the embodiments described above. The access device 400 comprises a cannula 410 and a seal assembly 420. The seal assembly 420 comprises a seal housing 430 and a cap 440. An instrument seal 450 and a zero seal 490 are disposed within the seal housing 430. The instrument seal 450 comprises an orifice 452, a compression element 460, and an instrument contact element. The compression element 460 comprises a gel disc comprising an opening 466. The instrument contact element comprises a tubular membrane 482 extending through the opening 466 of the compression element. The membrane 482 comprises a first end and a second end, both of which are disposed proximal of the compression element 460, thereby "wrapping" and securing the compression element 460 therein.

FIGS. 5-9 illustrate other embodiments of compression elements that are useful in the access devices described and illustrated herein, as well as in other embodiments, as would be understood by those skilled in the art.

FIG. 5 is a top view of another embodiment of a gel disc compression element 560 in which the opening 566 is star shaped. The points of the star accommodate one or more of the folds or pleats in the membrane of the instrument contact element, thereby improving sealing to smaller diameter instruments and/or in the absence of an instrument. In some embodiments, the slits or cut out sections in the opening 566 permit the use of a thicker membrane and/or a lower elongation material for the compression element 560, either or both of which improves the overall durability of the instrument seal.

Some embodiments of the opening 566 have a different shape at a proximal end and a distal end thereof. Differences in a fold pattern in the membrane between the proximal end and distal end, and/or within the opening 566 can reduce the leak rate of the instrument seal by reducing or removing the gas leak paths.

FIG. 6 is a perspective view of another embodiment of a compression element 660 comprising a gel torus or donut.

The opening 666 is narrower at a center thereof, and wider at both ends. The rounded or arcuate opening 666 at the proximal and distal ends also reduces a strike plane of the compression element 660, thereby reducing potential cuts or penetrations of the membrane.

FIGS. 7A, 7B, and 7C are top, side, and cross-sectional views of another embodiment of a frustoconical gel compression element 760. The compression element 760 converges from a first end to a second end, terminating in an opening 766. In the illustrated embodiment, the first end of the compression element is reinforced with a ring 762 of gel material. The opening 766 is also comprises a ring 764 of gel material. The illustrated embodiment is useful as the compression element, for example, in the embodiment illustrated in FIGS. 2, 3, and 4.

Figure 8A:
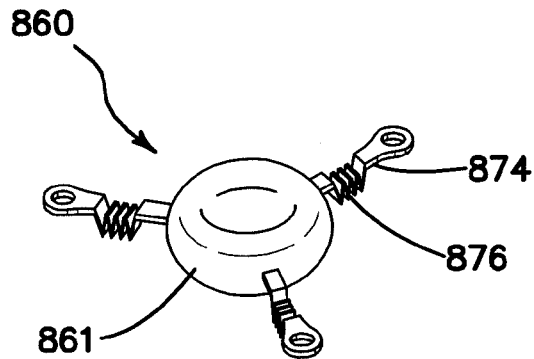
FIGS. 8A and 8B are perspective and top views of an embodiment of a compression element comprising a torus and a plurality of tethers.
Figure 8B:
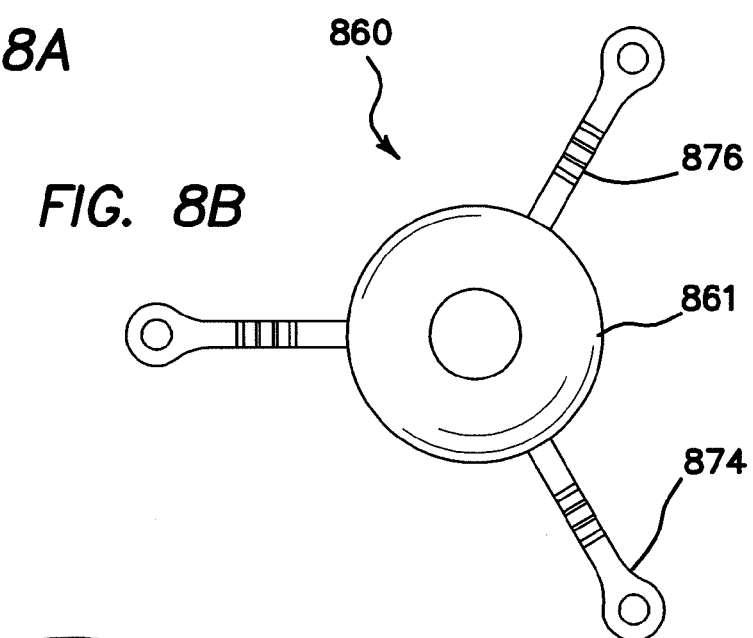

FIGS. 8A and 8B are perspective and top views of an embodiment of a compression element 860 comprising a gel torus 861 similar to the embodiment illustrated in FIG. 6 and a plurality of radially extending tethers 874, which secure the compression element 860, for example, to the seal housing, thereby providing more precise instrument tracking. Embodiments of the tethers 874 also restrict longitudinal or axial movement of the torus 861, thereby further reducing hysteresis. Each of the tethers 874 in the illustrated embodiment comprises a pleated portion 876 that accommodates lateral movement of the torus 861. In some embodiments, the torus 861 and tethers 874 comprise the same material. In some embodiments, the torus 861 and tethers 874 are monolithic. In other embodiments, the torus 861 and tethers 874 comprise different materials, for example, a gel torus 861 and tethers 874 comprising a more rigid material.

Figure 9:
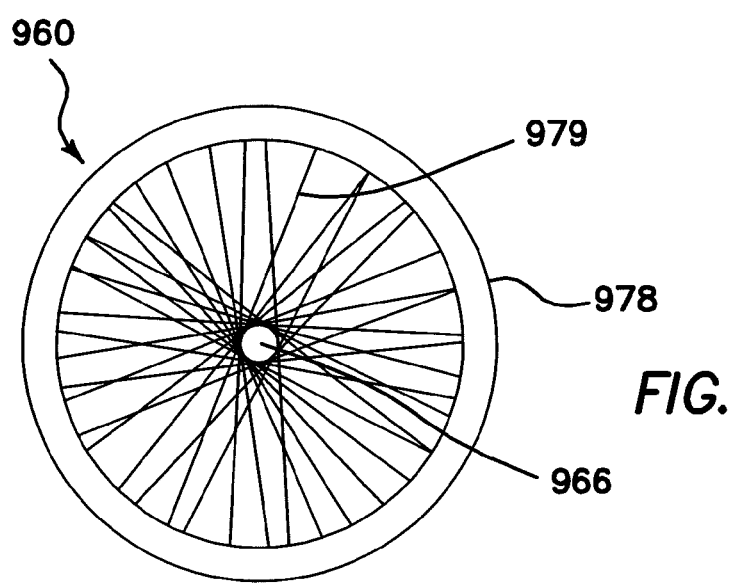
FIG. 9 is a top view of an embodiment of a compression element comprising a rim and a plurality of elastic elements.

FIG. 9 is a top view of an embodiment of a compression element 960 comprising a circular rim 978 and a plurality of elastic elements or bands 979 arranged as chords across the circular rim 978, each rotated with respect to a longitudinal axis of the compression element 960. Each elastic element 979 overlaps at least one other elastic element 979. In some embodiments, the elastic elements 979 are arranged symmetrically. The elastic elements 979 comprise any suitable elastomeric material, for example, gel, rubber, elastomeric polymer, and the like. The plurality of elastic elements 979 together defines an opening 966 in the compression element through which an instrument contact element is disposed as discussed above. In other embodiments, the rim 978 has another shape, for example, oval or polygonal.

Some embodiments of the access device comprise a plurality of compression elements disposed along a length of a single instrument contact element. In some embodiments, the shape, dimensions, and/or properties of the compression elements are selected to improve one or more properties, for example, sealing a wider range of instrument diameters, achieving a more constant drag force, and/or reducing leakage with no instrument in the instrument channel.

In some embodiments, the entire instrument seal is movable within the seal housing, thereby providing additional float to the instrument seal. In some of these embodiments, the instrument seal exhibits improved sealing with off axis and/or angled instruments.

Embodiments of the instrument seal do not comprise actuators, dilators, or expander used in some instrument seals to pre-dilate the seal, or any movable shields or protectors that pre-dilate and/or protect the instrument seal. The membrane does not define a closed cavity or bladder in which air or an injected fluid defines or constricts the orifice of the seal, as well as restricting movement of the seal, for example, side-to-side motion.

While certain embodiments have been particularly shown and described with reference to exemplary embodiments thereof, it will be understood by those of ordinary skill in the art that various changes in form and details may be made therein without departing from the spirit and scope thereof as defined by the following claims.

What is claimed is:

1. A surgical access device comprising:
   a seal housing;
   an elastic compression element disposed in the seal housing;
   a non-distensible instrument contact element extending through an opening in the compression element and a distal end of the instrument contact element positioned below the opening is secured to a disc weight; and
   a tensioning element urging the disc weight distally, wherein the tensioning element is at least one of a spring, an elastic band and a balloon.

2. The surgical access device of claim 1 wherein the instrument contact element comprises at least one slit.

3. The surgical access device of claim 1 wherein the elastic compression element is a zero seal in the absence of an instrument extending through the instrument contact element.

4. The surgical access device of claim 1 wherein in the absence of an instrument extending through the instrument contact element, the instrument contact element at the opening in the compression element comprises a plurality of folds.

5. The surgical access device of claim 1 wherein in the presence of an instrument extending through the instrument contact element and the opening of the compression element, the instrument contact element seals against the instrument and spaces the instrument from the compression element.

6. The surgical access device of claim 1 wherein the instrument contact element comprises a polyolefin film.

7. The surgical access device of claim 1 further comprising a cannula extending from the seal housing.

8. The surgical access device of claim 1 further comprising a zero seal.

9. The surgical access device of claim 1 further comprising a stop limiting proximal movement of the disc weight.

10. The surgical access device of claim 1 wherein the compression element comprises a plurality of elastic elements defining an opening through which the instrument contact element extends, wherein at least some of the plurality of elastic elements overlap at least one other elastic element.

11. The surgical access device of claim 1 wherein the compression element is disc-shaped.

12. The surgical access device of claim 1 wherein the compression element is tethered to the seal housing.

13. The surgical access device of claim 1 wherein the disc weight is movable within the seal housing.

14. The surgical access device of claim 1 wherein the compression element has a proximal terminal end and the instrument contact element has a proximal terminal end, the proximal terminal end of the compression element being positioned above the proximal terminal end of the instrument contact element.

15. The surgical access device of claim 1 wherein the instrument contact element has a proximal terminal end connected to an inner wall of the compression element.

16. The surgical access device of claim 1 wherein the compression element has a proximal end extending and tapering distally to a distal end in which the opening is disposed therein.

17. The surgical access device of claim 16 wherein the instrument contact element has a proximal end secured to the proximal end of the compression element.

18. The surgical access device of claim 1 wherein the compression element has a proximal end having a diameter and the opening in the compression element having a diameter smaller than the diameter of the proximal end of the compression element.

19. The surgical access device of claim 18 wherein the instrument contact element has a proximal end secured to the proximal end of the compression element.

\* \* \* \* \*